United States Patent
Li et al.

(10) Patent No.: US 10,234,392 B2
(45) Date of Patent: *Mar. 19, 2019

(54) OPTICAL ENGINE FOR FLOW CYTOMETER, FLOW CYTOMETER SYSTEM AND METHODS OF USE

(71) Applicant: ACEA Biosciences, Inc., San Diego, CA (US)

(72) Inventors: Nan Li, San Diego, CA (US); Ye Chen, Hangzhou (CN); Hyunsun Chung, Weston, FL (US); Zengqiang Li, Hangzhou (CN); Xiaobo Wang, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/416,976

(22) Filed: Jan. 26, 2017

(65) Prior Publication Data

US 2017/0138856 A1    May 18, 2017

Related U.S. Application Data

(63) Continuation of application No. 14/547,963, filed on Nov. 19, 2014, now Pat. No. 9,575,063.
(Continued)

(51) Int. Cl.
*G01N 21/64* (2006.01)
*G01N 33/569* (2006.01)
(Continued)

(52) U.S. Cl.
CPC ....... *G01N 21/645* (2013.01); *G01N 15/1434* (2013.01); *G01N 15/1459* (2013.01);
(Continued)

(58) Field of Classification Search
CPC ....... G01N 15/1434; G01N 2021/6471; G01N 2021/6478; G01N 21/645; G01N 21/6486; G01N 2201/06113
See application file for complete search history.

(56) References Cited

U.S. PATENT DOCUMENTS 4,482,994 A    11/1984   Ishikawa
4,573,796 A     3/1986   Martin et al.
(Continued)

FOREIGN PATENT DOCUMENTS

CN       102087198        6/2011
WO    2003/021241 A1      3/2003
(Continued)

OTHER PUBLICATIONS

EP14863825 Supplementary European Search Report dated Jul. 26, 2017.
(Continued)

*Primary Examiner* — Tri T Ton
(74) *Attorney, Agent, or Firm* — Wagenknecht IP Law Group PC

(57) ABSTRACT

An optical engine for use in a bench top flow cytometer, the optical engine comprising a set of lasers; a different set of beam shaping optics for each laser, wherein each set comprises two lenses to adjustably focus light horizontally along an x-axis to a same horizontal position and vertically along a y-axis to a different vertical position along a same plane; collection optics for collecting fluorescence from the flow cell; filtration optics that filter the collected fluorescence from the flow cell into different detection channels according to wavelength ranges; and a detector for each detection channel that converts the filtered fluorescence to electrical signals, wherein electrical signals are processed so that the
(Continued)

fluorescence from each laser at the different vertical positions is distinguished at the same detector.

20 Claims, 23 Drawing Sheets

Related U.S. Application Data

(60) Provisional application No. 61/994,980, filed on May 18, 2014, provisional application No. 61/906,367, filed on Nov. 19, 2013.

(51) Int. Cl.
*G01N 15/14* (2006.01)
*G01N 15/10* (2006.01)

(52) U.S. Cl.
CPC ... *G01N 21/6486* (2013.01); *G01N 33/56972* (2013.01); *G01N 2015/1006* (2013.01); *G01N 2015/1402* (2013.01); *G01N 2015/1438* (2013.01); *G01N 2015/1477* (2013.01); *G01N 2021/6471* (2013.01); *G01N 2021/6478* (2013.01); *G01N 2201/06113* (2013.01)

(56) References Cited

U.S. PATENT DOCUMENTS

| | | | |
|---|---|---|---|
| 4,707,064 | A | 11/1987 | Dobrowlski et al. |
| 4,727,020 | A | 2/1988 | Recktenwald |
| 5,674,698 | A | 10/1997 | Zarling et al. |
| 5,760,900 | A | 6/1998 | Ito et al. |
| 5,865,520 | A | 2/1999 | Kavanagh et al. |
| 5,930,048 | A | 7/1999 | Kaneko |
| 6,294,063 | B1 | 9/2001 | Becker et al. |
| 6,404,493 | B1 | 6/2002 | Altendorf |
| 6,510,007 | B1 | 1/2003 | Blasenheim |
| 6,558,945 | B1 | 5/2003 | Kao |
| 7,110,192 | B2 | 9/2006 | Sauter et al. |
| 7,523,637 | B2 | 4/2009 | Roth et al. |
| 7,738,099 | B2 | 6/2010 | Morrell et al. |
| 7,758,811 | B2 | 7/2010 | Durack et al. |
| 7,777,869 | B2 | 8/2010 | Nerin et al. |
| 7,952,806 | B2 | 5/2011 | Callen et al. |
| 8,077,310 | B2 | 12/2011 | Olson et al. |
| 8,101,426 | B2 | 1/2012 | Durack et al. |
| 8,619,370 | B2 | 12/2013 | Hunter et al. |
| 8,791,429 | B2 | 7/2014 | Kim et al. |
| 8,883,495 | B2 | 11/2014 | Nakamura et al. |
| 9,158,118 | B2 | 10/2015 | Li et al. |
| 9,423,348 | B2 | 8/2016 | Norton |
| 9,568,423 | B2 | 2/2017 | Li et al. |
| 9,575,063 | B2 | 2/2017 | Li et al. |
| 2007/0096039 | A1 | 5/2007 | Kapoor et al. |
| 2008/0213915 | A1 | 9/2008 | Durack et al. |
| 2008/0283754 | A1 | 11/2008 | Nerin et al. |
| 2009/0141327 | A1 | 6/2009 | Penn et al. |
| 2010/0220315 | A1* | 9/2010 | Morrell .............. G01N 15/1436 356/73 |
| 2010/0322064 | A1 | 12/2010 | Kim et al. |
| 2013/0200277 | A1 | 8/2013 | Li et al. |
| 2015/0140577 | A1 | 5/2015 | Li et al. |
| 2016/0097707 | A1 | 4/2016 | Li et al. |
| 2017/0131206 | A1 | 5/2017 | Li et al. |

FOREIGN PATENT DOCUMENTS

| | | |
|---|---|---|
| WO | 2010/099118 A1 | 9/2010 |
| WO | 2011003073 A1 | 1/2011 |
| WO | 2011/140153 A1 | 11/2011 |
| WO | 2013059835 A1 | 4/2013 |
| WO | 2015077349 A2 | 5/2015 |

OTHER PUBLICATIONS

EP12845835.3 European Search Report dated Jul. 1, 2015.
EP12841762.3 Extended European Search Report dated Mar. 27, 2015.
PCT/US2014/006429 International Search Report and Written Opinion dated Mar. 23, 2015.
Ramirez, et al. "High-Throughout Flow Cytometry: Validation in Microvolume Bioassays." Cytometry Part A, 2003, 53A:55-65, Wiley-Liss Inc.
Scientiis International "Coming and Costar 96-well Cell Culture Plates" available on the company's webpage for product information, copyright 2005. http://scientiis.com/laboratorium/catalog/product_info.php?products_id=5574. retrieved from the internet on Dec. 9, 2016.
PCT/US2017/042284 International Search Report and Written Opinion dated Oct. 6, 2017.
PCT/US2012/061399 International Search Report dated Jan. 9, 2013.

\* cited by examiner

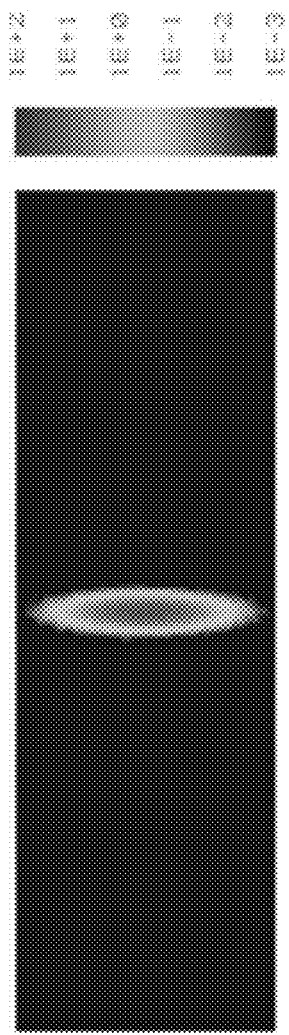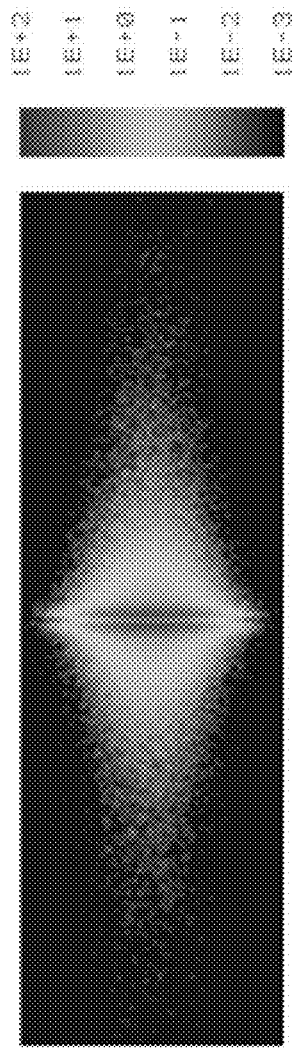
FIG. 8A
FIG. 8B

OPTICAL ENGINE FOR FLOW CYTOMETER, FLOW CYTOMETER SYSTEM AND METHODS OF USE

CROSS REFERENCE TO RELATED APPLICATIONS

This application is a continuation of U.S. patent application Ser. No. 14/547,963, filed Nov. 19, 2014, which claims benefit of priority to U.S. provisional patent application Ser. No. 61/906,367, filed Nov. 19, 2013 and U.S. provisional patent application Ser. No. 61/994,980, filed May 18, 2014; the entire content of which is herein incorporated by reference in its entirety.

TECHNICAL FIELD

The invention relates to flow cytometry instrumentation and more specifically to an optical engine with interchangeable components for a flow cytometer having beam shaping optics for each laser that vertically position the excitation laser beam at different positions along the flowing direction of the measured sample and a set of filtration optics that filter fluorescence from the different vertical positions into a plurality of filter channels, where fluorescence from each vertical position can be individually measured by a same detector.

BACKGROUND OF THE INVENTION

Flow cytometry is a laser-based, biophysical technology where fluorescent molecules coupled to cells are passed through a flow cell and excited by a set of lasers. The fluorescence is collected and separated into different channels with specific detection wavelength, converted to electrical signals, and analyzed using a computer. Multi-color flow cytometry, such as three color flow cytometry uses fluorophores with different excitation and emission wavelengths for identification of different staining of the biological samples. More specifically, the excitation light is delivered to the flow cell by beam-shaping, steering, and guiding optical components. Conventionally, such components are arranged so that light from all lasers pass through a same set of beam shaping, steering and guiding components before reaching the flow cell. Such beam shaping optics can include, for example, achromatic lenses (cylindrical or spherical) to accommodate different wavelengths of different lasers. In addition, the beam-steering/guiding components direct all light beams to the center of the flow cell, either at a same position or at different positions along the flowing direction of the sample. However, a limitation of this approach is that by providing a same set of optics for the set of lasers, the beam shaping and beam guiding components are compromised in that they shape and steer light beams of different wavelengths for somewhat sub-optimum beam sizes to sub-optimum focus-locations. Thus, there is a need for an approach to optical illumination that improves beam size and focusing point. In addition, the beam size and focusing point should be able to be adjusted independently for each laser.

In addition to fluorescence, two other types of light scatter are measured in flow cytometery, namely side scatter and forward scatter. Forward scatter (FSC) is considered a low angle scatter and is roughly proportional to the diameter of the cell. Therefore FSC is useful in identifying certain cell subpopulations from others based on cell size. Since forward scatter is typically measured along a same path as beam propagation, an optical beam obscuration bar is conventionally added behind the flow cell but along the optical path of laser beam propagation to block the unscattered, high-intensity raw laser beam. A challenge in obscuration bar design is that it should block the unscattered raw laser beam but permit passage of low angle forward scattered light for detection. Conventionally, the obscuration bar is either rectangular or cross-shaped. Such geometry is generally designed empirically, with some geometries blocking too much forward scatter light yet other designs lacking sufficient blocking of unscattered light. Therefore, there is also a need for an improved optical beam obscuration bar that improves the balance of blocking unscattered light while permitting passage of forward scatter light.

In another flow cytometer, fluorescent light is collected from the particles (e.g. cells) flowing through the center of the flow cell. Complex design including multiple-lenses positioned at accurate locations relative to each other and relative to flow cell is employed to collect fluorescent light from the particles. Such collection optics is expensive to make, difficult to align and adjust. For many situations, the light collection efficiency is limited. Therefore, there is also a need for an improved collection optics that is simple in design, comprising fewer optic components and has high light-collection efficiency.

SUMMARY OF THE INVENTION

The above deficiencies in flow cytometry design and technical approach are addressed by the present invention. In one aspect of the invention, an optical engine for use in a flow cytometer is provided, the optical engine including: a set of lasers, each tuned to a wavelength suited for excitation of fluorescent molecules; a set of beam shaping optics for each laser, wherein each set comprises two lenses to adjustably focus light horizontally along an x-axis to a same horizontal position and vertically along a y-axis to a different vertical position along a same plane, wherein the plane is characterized as a flow path through a flow cell of the flow cytometer; collection optics for collecting fluorescence from the flow cell; filtration optics that filter the collected fluorescence from the flow cell into different filter channels according to wavelength ranges; and a detector for each filter channel that converts the filtered fluorescence to electrical signals, wherein electrical signals are processed so that the fluorescence from each laser at the different vertical positions is distinguished at the same detector. For the present application, light propagation direction for each laser is defined as Z-axis, which is perpendicular to the horizontal x-axis and to the vertical y-axis.

The optical engine permits the use of any number of lasers, but in some embodiments has at least three lasers, which are each tuned to a different wavelength and focused to a different vertical position of the flow cell. Vertically focusing each of the at least three lasers individually at different vertical positions along a flowing direction of the sample allows the possibility for distinguishing fluorescence excited by each of the three different lasers by the same photodetector, as the spatial separation of the three different lasers along the vertical axis would translate to temporal differences in fluorescence emitted by particles when passing through each of the three different lasers. Distinguishing and separating fluorescent signals at the same detector from different excitation lasers is of critical importance in the present invention where the same detector is shared by different fluorescence signal detection channels from different excitation lasers. The separation of laser focal points along the flow cell leads to a time delay in detected fluorescent signals excited by spatially separated lasers. With the reference of the forward scatter emission from one particular laser, the timing delay of the fluorescent signals would be a fixed number determined by the separation distance of the lasers and the flowing velocity of the detected sample, which allows the relationship between detected fluorescence signal and the corresponding excitation laser to be identified. In other approaches, different lasers are temporally modulated at different frequencies. Demodulation of the electrical signals (which are converted from fluorescence light) by corresponding modulation signals would make it possible to correlate the detected fluorescence with an excitation laser. The detailed apparatus, method and techniques for the modulation of laser sources and demodulation of collected electrical signals (after conversion from the fluorescent lights) can be found in a previous patent application titled "System and Method for Detecting Multiple-Excitation Induced Light in a Flow Channel", having a U.S. patent application Ser. No. 13/657,845, which is incorporated by reference in its entirety. In some embodiments, the vertical separation between neighboring vertical positions is 80 µm. In an exemplary embodiment, the collection and analysis of 10 fluorescence signals from a single sample passing through the flow cell has been achieved. In another embodiment, collection of 13 fluorescence signals can be obtained from a single sample passing through the flow cell in addition to forward and side scatter measurement. To emphasize one important feature of the present invention, detectors for measuring and converting the fluorescent light are shared between fluorescent channels from different excitation lasers.

The optics of the optical engine include beam shaping optics, collection optics and filtration optics. In a preferred embodiment, the set of beam shaping optics comprise a cylindrical lens or a Powell lens. In a preferred embodiment, the collection optics include a half ball lens followed by a doublet lens. Preferably, the half-ball lens is made of the materials having a high refractive index. The filtration optics and can include long pass and/or short pass dichroic mirrors, bandpass filters, focusing lenses and other filters or lenses. In some embodiments, the filtration optics filter the collected fluorescence light by the half ball lens and the doublet lens into detection channels characterized as the following wavelengths 780/60 nm, 615/24 nm, 530/30 nm, 445/45 nm, 585/40 nm (or 572/28 nm) and 675/30 nm. Note that all the wavelengths have a unit of nm. The channel wavelengths cited here are for exemplary purposes only and are not intended for limiting the present invention.

A detector is provided for each filter channel, which is preferably in the form of a photomultiplier tube. Preferably, fluorescent light signal is converted to an analog electrical signal. Still preferably, analog signals are then converted to digital signals using analog to digital converter (ADC) and processed in digital form for increased accuracy and speed.

In a preferred embodiment, forward scatter (FSC) characterization of cells includes a FSC detector, a FSC focusing lens to collect FSC light, and an obscuration bar that blocks an incident laser beam from entering the FSC focusing lens and the FSC detector. The relationship between timing of fluorescence signal at a fluorescent light detector and timing of forward scatter signal at a FSC detector provides an approach for determining which laser induces excitation of a detected fluorescent signal in a detection channel. Further, improving forward scatter detection has been accomplished through the development of new obscuration bars. In a preferred embodiment, a diamond shaped obscuration bar is provided. In another embodiment an obscuration bar that is of a rectangular shape and has its horizontal dimension being the same as or longer than its vertical dimension is provided for blocking the incident laser beam. In still another embodiment, the perimeter of the obscuration bar follows a contour of a light intensity distribution plot for blocking incident laser beam. In a still further embodiment, the obscuration bar follows a contour of a light intensity distribution plot within the 0.1% contour line. A 0.1% contour line or boundary corresponds to a line where the light intensity at each point on the contour is at 0.1% of maximum light intensity of the incident light. An obscuration bar following the contour of a light intensity distribution plot within the 0.1% contour was determined to block 99% of the unscattered beam from the FSC detector. Accordingly, the invention also provides an obscuration bar generally diamond shaped that follows a contour of a light intensity distribution plot within the 0.1%, 0.2%. 0.5%, 1.0% or 2.0% contour line and methods of its shaping.

Components of the optical engine are preferably housed as a single unit, which can be removed and interchanged for modification with other components. To this end, a housing configured to house optical engine components is also provided. The housing includes the optical engine components such as the set of lasers, beam shaping optics, collection optics, filtration optics, detectors, further filters and lenses as well as an electrical interface for electrical connection to electrical circuitry, which would be connected to an external microprocessor or a remote computer. Preferably, the components within a same housing are configured for interchangeability of different lasers, focusing lenses, long pass and short pass dichroic mirrors, filters, pinhole passages and detectors. This is accomplished by standardizing engagement features such as positioning of alignment holes, snaps, screws or other fasteners across different components for interchangeability and by providing a set of beam shaping optics for each laser individually. In some embodiments, a flow channel is mounted in the housing and configured for coupling to a flow cytometer apparatus for hydrodynamic focusing of samples including particles (e.g. beads or cells) by tubing connectors.

In a related embodiment, the invention also includes a flow cytometer, which includes any of the optical engines as disclosed herein; a flow channel; and a pump in fluid communication with an aspiration needle for aspirating and delivering a suspension of cells through the flow channel. In a preferred embodiment, the flow cytometer is further characterized in that there are at least three lasers, each tuned to a different wavelength and focused to a different vertical position of the flow cell; collection optics for collecting light from the flow cell; and filtration optics that spatially distinguish the filtered fluorescence in a same channel based on vertical position of the focused excitation beam. To the end, a flow cytometry apparatus is provided which includes up to 10 or 13 fluorescent color channels from a single sample passing through the flow cell in addition to side scatter and forward scatter measurement.

In a related embodiment a flow cytometry system has been developed, which includes a flow cytometer as provided herein; and a software for loading and execution in a computer to acquire and analyze flow cytometry data. As such, flow cytometry software for loading in a computer has also been developed. In some embodiments, the software provides programming to perform the following functions collecting data from fluorescence channels for each detector, wherein the fluorescence signals collected by a same detector are converted to different data series, corresponding to the fluorescence excited by lasers at the different vertical positions; generating a graphical user interface (GUI) that displays various plots for the acquired data, wherein the GUI further comprises compensation scroll bars adjacent to the comparison plots to adjust compensation of spectral overlap between one or more channel; acquiring the data from the cytometer and saving the data as a data file into the computer hard drive. The software also includes a gating function that permits the user to select a subpopulation from a data plot and generate additional plots for the selected subpopulation. This process can be performed repetitively for all fluorescence channel data as well as side scatter and forward scatter data.

In still another related embodiment a flow cytometry method is provided, which includes providing flow cytometry system as provided herein; labeling a suspension of cells with a plurality of fluorescent labels; pumping the sample of cells through the flow cell; collecting flow cytometry data; and analyzing the flow cytometry data to determine the presence, absence or abundance of one or more of the plurality of fluorescent labels on or in cells of the sample.

BRIEF DESCRIPTION OF THE DRAWINGS

FIGS. 8A-B show light intensity plots at the obscuration bar location for a flow cell illuminated with a focused, elliptical laser beam at the center of the flow channel for the cases of without (FIG. 8A) and with (FIG. 8B) a hydrodynamically (HD) focused core, wherein the HD core shown is a flow path of about 17 μm. In FIG. 8A, the flow channel is filled with sheath fluid everywhere. In FIG. 8B, the flow channel is filled with sheath fluid with a central region being a hydrodynamic focused core wherein the refractive indexes of the core is different from the refractive index of the sheath fluid.

DETAILED DESCRIPTION OF PREFERRED EMBODIMENTS

Figure 1A:
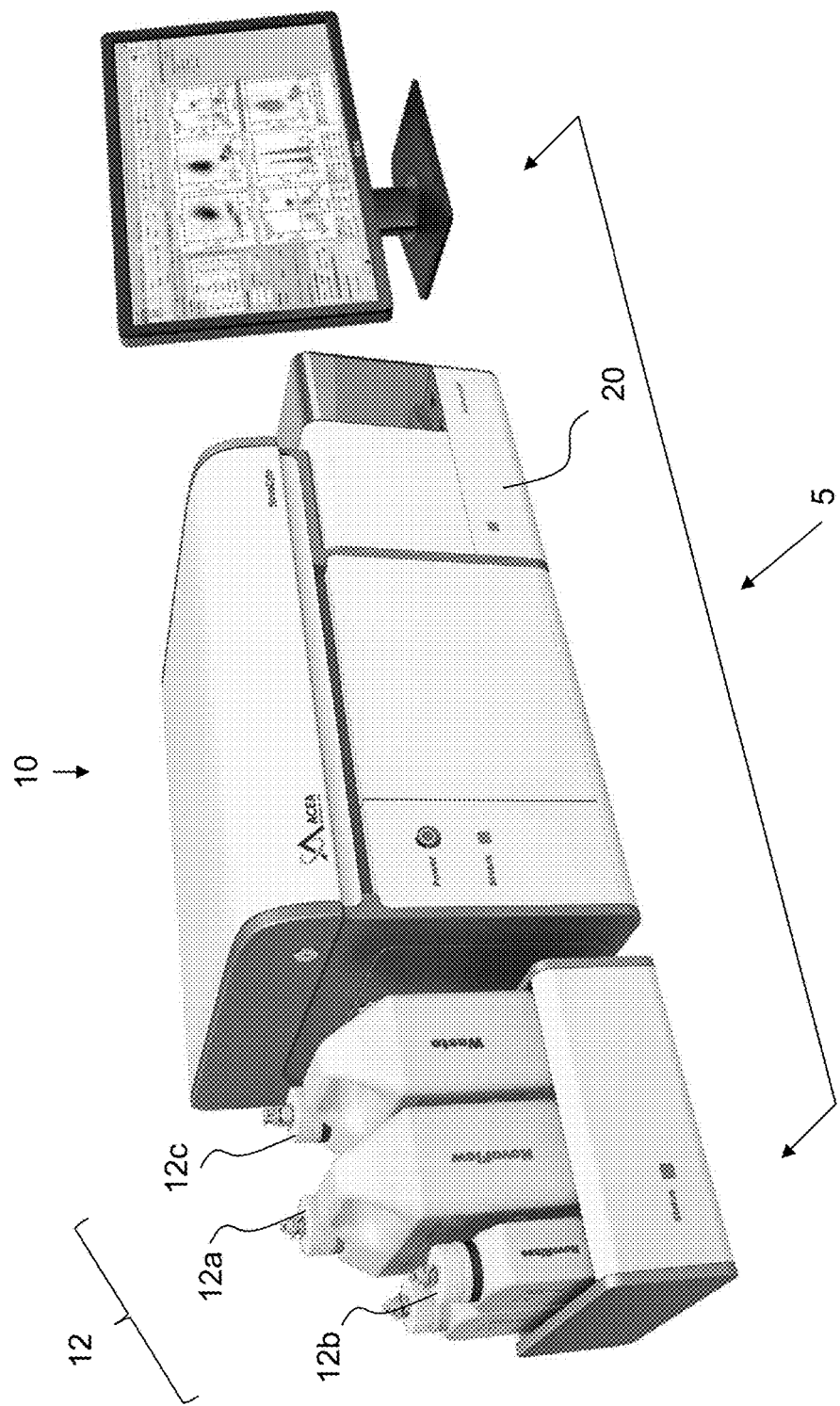
FIG. 1A is a picture of an exemplary flow cytometry system 5 including flow cytometer 10 with optional autosampler 20.

The invention provides a flow cytometer that incorporates an optical engine that is individually configurable and expandable by interchangeable lasers, optics configurations and detectors that provide measurement of up to 15 parameters, which results in 13 color fluorescence channels, of a single sample. The interchangeability of the components within the optical engine permits the user to tailor the excitation and detection channels according to unique experimental conditions and according to individual needs. This allows the user to add or substitute components within a same flow cytometer while maintaining high detection sensitivity and resolution.

To this end our testing of the flow cytometer demonstrated high sensitivity, resolution and accuracy. Further, the flow cytometer is shown to provide reliable direct absolute cell counts usable for diagnosis or monitoring of medical conditions having variations in cell subpopulations, such as human immunodeficiency virus (HIV), without the use of expensive reference beads common to other commercially available systems. Remarkably, the features have been incorporated into a bench top system.

The flow cytometer, includes an optical engine, which is described in various nonlimiting embodiments herein; a flow channel; and a pump in fluid communication with an aspiration needle for aspirating and delivering a suspension of cells through the flow channel. The pump fluidics are shown to reproducibly deliver cells through the flow channel at high speed to reproducibly conduct sample acquisition rates of over 35,000 events/second. Further, with the add-on autosampler and optional shaker, such rates can be achieved together with automated sample feeding to the aspiration needle. In addition, the flow cytometer is programmed with features such as autocleaning of the aspiration needle to reduce likelihood of sample carryover and cross-contamination.

In a preferred embodiment, the optical engine within the flow cytometer is further characterized as having a set of lasers, such as from one to three, each tuned to a different wavelength suited for excitation of fluorescent molecules. Improved focusing of each of the plurality of laser beams to distinct locations along the flow cell is accomplished by providing a set of beam shaping optics for each laser, wherein each set preferably includes two lenses to adjustably focus light horizontally along an x-axis to a same horizontal position and vertically along a y-axis to a different vertical position along a same plane, the plane characterized as being within a flow path through a flow cell of the flow cytometer. For the beam shaping optics described here, the laser light propagation direction is defined as Z-axis, which is normal to the horizontal x-axis and vertical y-axis. Beam shaping optics preferably include cylindrical lenses so that the focused beam is at the center line in the flow cell and of elliptical shape. By assigning beam shaping optics to each laser, each laser can be precisely focused to a different vertical position of the flow cell thereby eliminating the tradeoffs associated with configurations that require sharing beam shaping, steering and guiding optics between lasers as commonly provided in commercially available systems. Further, this precise focusing of lasers at distinct positions along the flow cell permits comparisons between the timing of fluorescence signals and forward scatter signals, which can be used to identify the relationship between detected fluorescence and excitation laser. Further, our filtration optics filter collected fluorescence from the flow cell into different filter channels according to wavelength ranges. And the detector at each filter channel converts the filtered light into electrical signals, wherein electrical signals are processed so that the light (fluorescent light) from each of the vertical positions of focused laser beans is distinguished at the same detector. The separation of laser focal points along the flow cell for different lasers leads to difference in timing of fluorescent signals. When compared to that for forward scatter emission from one particular laser, the timing of fluorescent signals would allow the relationship between detected fluorescence and excitation laser to be identified. For example, for a 3 laser system having red, blue and violet lasers, the laser beams are focused to 3 different vertical locations along the flow cell, in the order of first red, then blue and then violet counting from a lower position to a higher position. As particles (e.g. cells) moving through these 3 laser beams, for a given fluorescent light detector, the fluorescent light induced by red laser excitation would be ahead that induced by a blue laser, which is then followed by fluorescent light induced by a violet laser. Assuming that a forward scatter is detected for particles passing through the blue laser beam, the timing of forward scatter for a particle would coincide with fluorescence induced by blue laser. Signal processing approaches and algorithms can be developed for assigning such forward-scatter-coinciding fluorescence light to blue laser excitation. Based on the speed of particle moving in the flow cell and vertical separation distance between lasers, the fluorescent light in a given time window ahead of blue-laser induced fluorescence could be assigned to red-laser excitation. Similarly, based on the speed of particle moving in the flow cell and vertical separation distance between lasers, the fluorescent light in a given time window after blue-laser induced fluorescence could be assigned to violet-laser excitation. In other approaches, different lasers are temporally modulated at different frequencies. For example, red laser may be modulated at a frequency of 4 MHz and violet laser may be modulated at a frequency of 2 MHz, whilst blue laser may be operated at a non-modulated constant power (CW) mode. Demodulation of the electrical signals from a same detector by 4 MHz modulation signal would derive fluorescence light induced by the red laser. Demodulation of the electrical signals from the same detector by 2 MHZ modulation signal would derive fluorescence light induced by the violet laser. Low-pass filtering of the electrical signals from the same detector would filter out any modulated signals due to red and violet lasers, leading to fluorescence signals due to excitation of blue laser. This example discussed here is for showing the operation principle of modulation and demodulation for distinguishing fluorescent light from different laser sources. Previous patent application titled "System and Method for Detecting Multiple-Excitation Induced Light in a Flow Channel", having a U.S. patent application Ser. No. 13/657,845, describes the apparatus, method and techniques for such modulation and demodulation of laser beams in a flow cytometer application. This application U.S. Ser. No. 13/657,845 is incorporated by reference in its entirety. The identification of fluorescence signals with corresponding laser excitation can be achieved through either forwardscatter-coincidence method or laser-modulation and fluorescence-demodulation method, or combination of both methods. This way, detection at each detector can be performed so that detected, filtered fluorescence signals are assigned to corresponding lasers, which are focused at different vertical positions along the flow cell.

The flow cytometer is preferably provided as part of a flow cytometry system, which includes computer software for acquiring and analyzing flow cytometry data. The flow cytometry software operably communicates the flow cytometer to a computer and provides a variety of easy to use features. Among these include slideable compensation scroll bars positioned adjacent to corresponding fluorescent channels on displayed data plots, an easy to use experiment manager, and improved laboratory reports showing gated populations and corresponding counts.

To the end, a preferred flow cytometry system includes configurable detection fluorescence channels; 1 to 3 lasers; optimized PMT voltage; automated fluid-maintenance functions; syringe pump sampling fluidic system; novel optical design, with enhanced signal detection as a powerful analytical tool for cell-by-cell discrimination. This system permits reliable quantitative measurements and rapid acquisition of statistically significant data for high density, multiplexed assays.

Figure 1B:
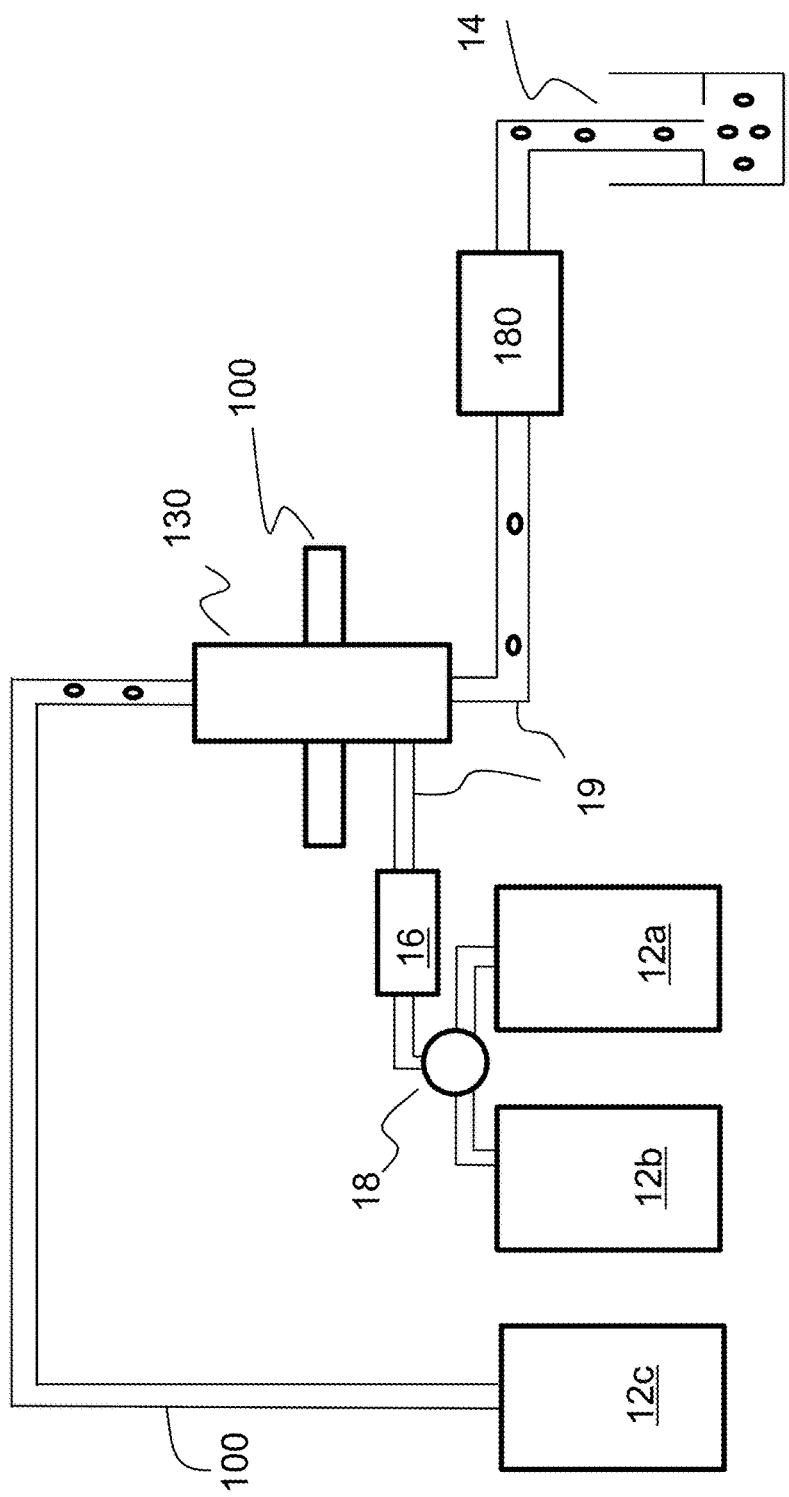
FIG. 1B is a schematic providing an overview of transfer of a cell suspension through the optical engine 100.
Figure 6:
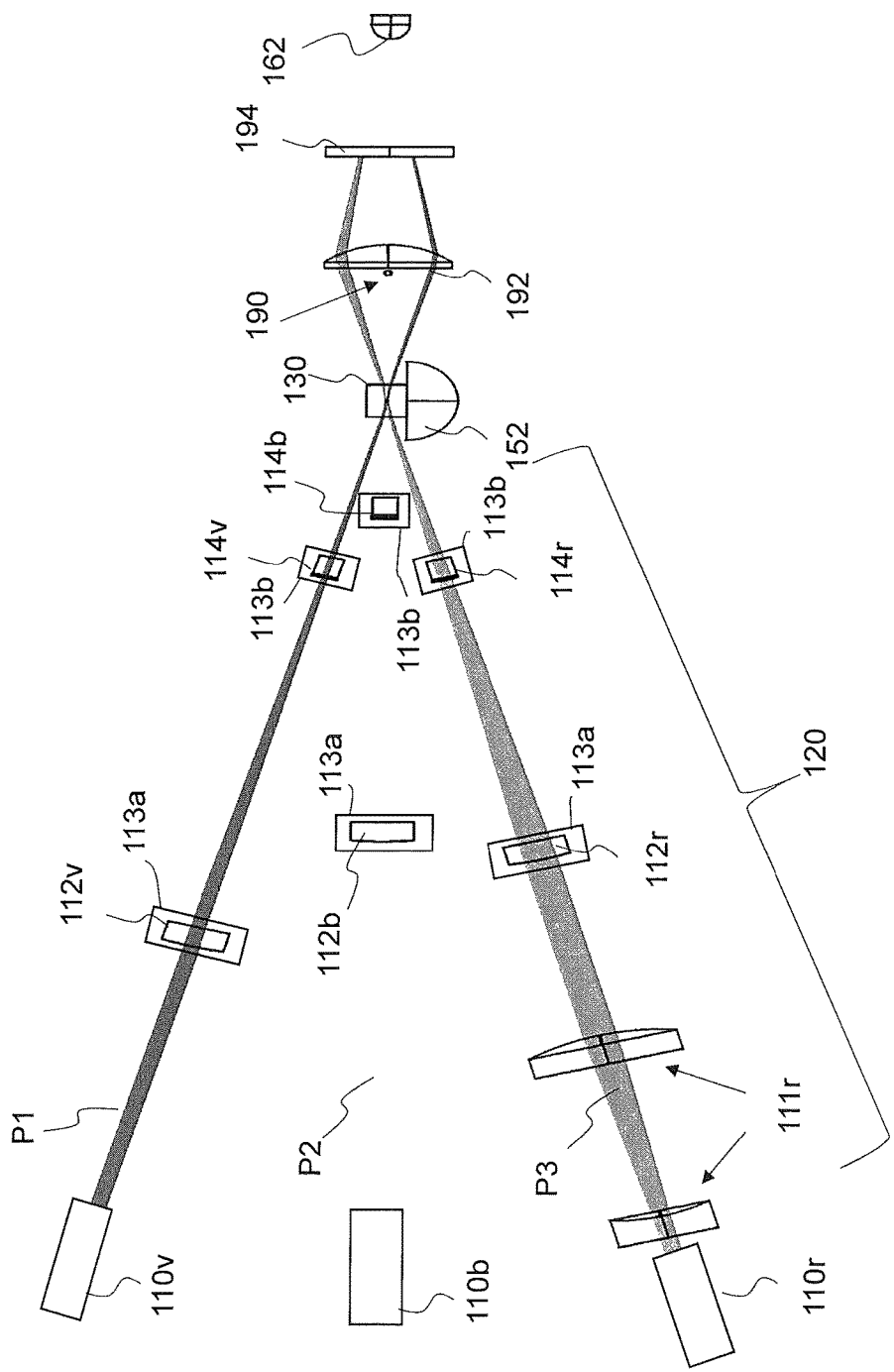
FIG. 6 is a schematic top view of showing laser light propagation along three light paths P1-3 along the Z-axis; wherein horizontal X-axis is normal to the direction of laser light propagation (i.e. Z-axis) of an optical illumination system including 3-laser excitation sources. Also shown is the blocking of unscattered light from path P2 by the obscuration bar 190.

Turning now to FIGS. 1A, 1B, and 6 a flow cytometry system includes the flow cytometer 10 in fluid communication with an aspiration needle 14 for aspirating a suspension of cells, and is in fluid communication with containers 12, such as a sheath fluid container 12a filled with sheath fluid; a rinse fluid container 12b filled with rinse fluid; and a waste fluid container 12c for delivering waste as known in the flow cytometry arts. The fluid containers 12 may be reusable or disposable and are connected to internal pumps 16. As an overview of operation shown in FIG. 1B, the pump 16 drives sheath fluid to the flow cell 130, into which sample is also delivered by other mechanisms such as a pump 180. The sample with a suspension of particles (e.g. cells) would be hydrodynamically focused by the sheath fluid into the center of the flow cell. The ordered passage of cells through different excitation lasers would result in generation of fluorescent light, which would detected by detectors following light collection and light splitting. There are various methods and approaches for driving and delivering of sheath fluid and sample fluids containing suspensions of cells into a flow cell for hydrodynamic focusing of sample fluid. These are well known in the flow cytometry arts and are typically accomplished using a combination of pumps 16, 180, valves 18 and flow passages 19.

Figure 2:
FIG. 2 is a picture of the autosampler 20.

The flow cytometer 10 can be operated manually such as by individually providing a suspension of cells tube-by-tube to the flow cytometer 10, through aspiration via a sample aspiration needle 14 (FIG. 1B) as known in the flow cytometry arts or as shown in FIGS. 1 and 2, may be adapted for high throughput through the incorporation of an optional modular autosampler 20. The modular autosampler 20 is compatible with different loading tubes. Among these include racks of conventional 12×75 mm flow tubes, 1.5/2.0 mL tubes, such as those commonly manufactured by Eppendorf International, multi-well plates, such as 24 well, 96 well, flat bottom, V-bottom, round bottom or any other suitable tube or dish for maintaining a suspension of cells. Testing has shown sample acquisition in less than 1 hr for a 96 well plate with a sample suspension of 10 µL per well using the autosampler 20. In preferred embodiments, the autosampler 20 is equipped with a shaker for sample agitation and mixing. In preferred embodiments the autosampler 20 includes self-alignment protocols for ease of setup and maintenance, allowing convenient installation by users.

In preferred embodiments the flow cytometer includes a microprocessor (i.e. one or multiple microprocessors) to control a variety of functions, such as fluid or sample delivery, cell suspension or shaking, and self-alignment of sample vessels. The microprocessor is typically provided on a circuit board, coupled to memory and electrically connected to electric mechanisms such as electric pumps and actuators to accomplish the intended function. Further, the microprocessor may modulate voltages to the detectors, lasers, aspirating pump or other electrical components. The microprocessor may determine a time of fluorescence detection within each channel and time of forward scatter detection of a same cell or particle to determine which laser induced excitation of the corresponding fluorophores for assignment to a corresponding color and thus reagent. The microprocessor may include an analog to digital converter for converting analog signals from the photodetectors to digital signals. The microprocessor is communicatively connected to a computer, which provides various control commands to the microprocessor and receives the data from the microprocessor, controlled by the developed software.

Preferred embodiments include executable control programs stored in the microprocessor for automated sample aspiration needle 14 cleaning (when a clean command is received from the computer connected to the cytometer) after every sample aspiration to reduce risk of cross contamination of cell suspensions. This is still more preferred when using the autosampler 20. This is accomplished by controlling various pumps and valves for cleaning external and internal surfaces of the aspiration needle(s) 14 with sheath fluid or rinse fluid. Testing of this feature has shown less than 0.05% carry over in embodiments using the autosampler 20.

Preferred embodiments also include an automated de-bubble and unclogging feature, which prevents erroneous results from bubbles or clogs in the fluidic flow of cell suspensions and further ensures accurate direct absolute counts without needs of expensive reference counting beads. In preferred embodiments, the flow cytometer also includes an automated cleaning function at start up and shut down of the flow cytometer. This programming improves the ease of use and removes the need of the user to perform these steps, which can be tedious and time consuming. In still further embodiments an automatic fluid level detection alarm, such as in the form of a suitable fluid-level sensor is incorporated to inform the user when system fluid levels are low.

Figure 3:
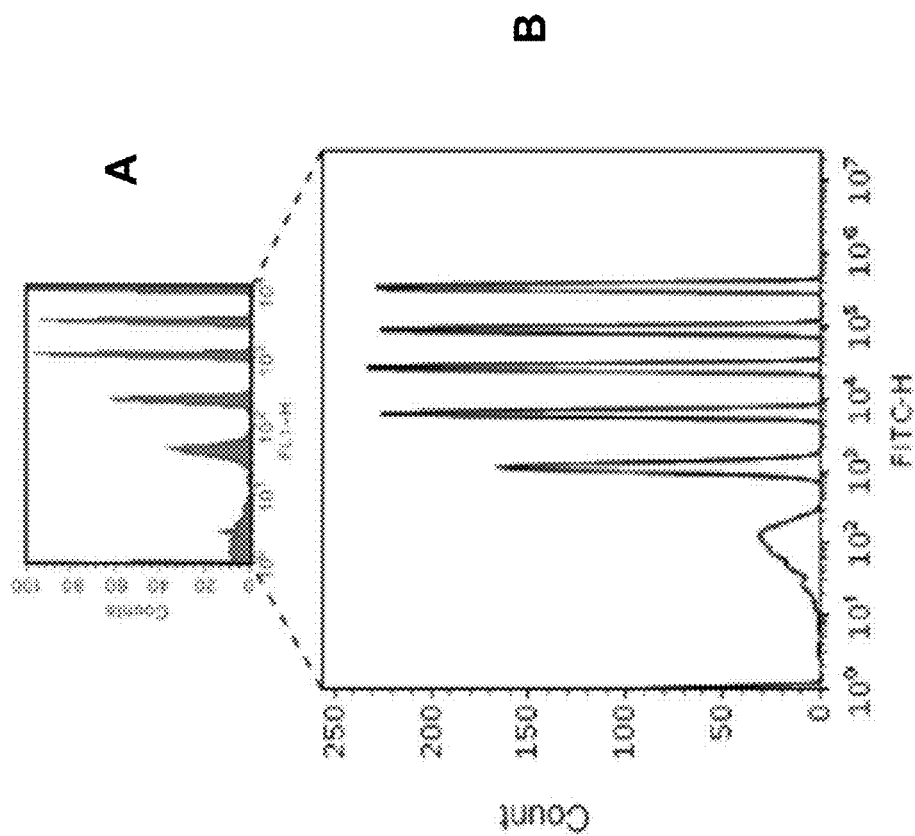
FIG. 3 is a plot showing counts as detected on a FITC channel (530/30 nm) obtained for a population of hard-dyed bead populations, consisting six different fluorescent intensities in both a competitor's flow cytometer (panel A) and our flow cytometery (panel B) to reveal our device and system provides a $10^7$ dynamic range for signal detection and processing, which is two orders of magnitude higher than other flow cytometers.

To demonstrate the improved data acquisition, resolution and ease of use our flow cytometer 10, we compared it to competitors' flow cytometers. FIG. 3 panel A depicts exemplary results from a competitor's flow cytometer and panel B shows results from our flow cytometer. FIG. 3 is representative of our findings in that our device and system provides a $10^7$ dynamic range for signal detection and processing, which can be two orders of magnitude higher than other flow cytometers. These results are achieved in part to our optics configuration and high quality PMT module, which ensures high sensitive fluorescence channel detection. While our system has improved sensitivity, it also eliminates the need for complicated and laborious PMT voltage adjustment. Instead data acquisition is just load-and-go. The high speed sample acquisition rates used in our system can be above 35,000 events/second. In addition, there is easy compensation during or post acquisition using scroll bars incorporated into the software.

Figure 4:
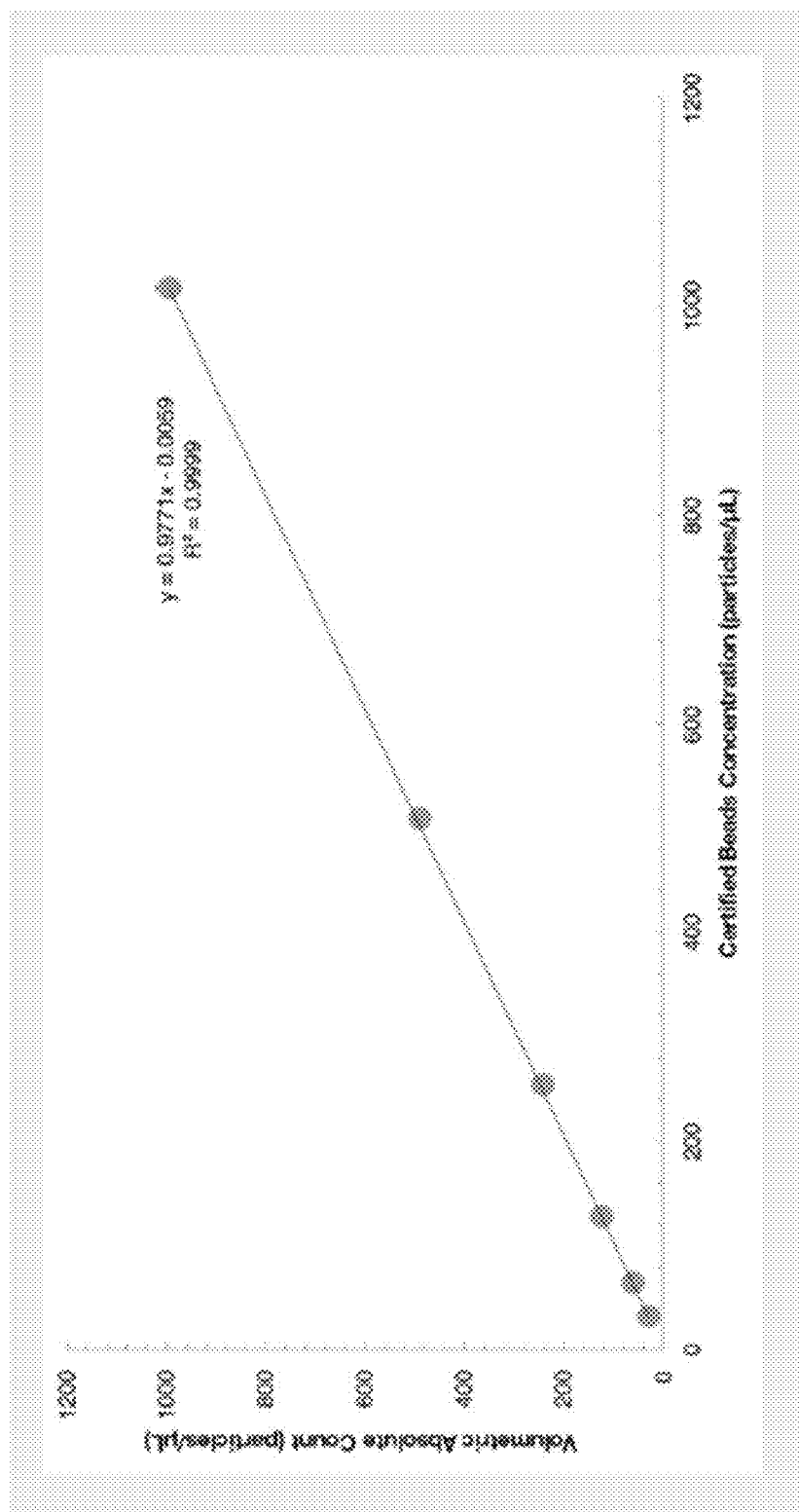
FIG. 4 is a graph showing the volumetric counts for certain beads as determined on our flow cytometer versus the expected bead concentrations, based on the certified concentration as well as the dilution factor. This plot shows an important feature of our cytometer where the volumetric syringe pump provides highly accurate and reproducible volume aspiration of samples.

FIG. 4 is a graph showing accuracy of volumetric absolute counting in our cytometers where the syringe pump (would be located underneath flow cell 130 in FIG. 5, but not shown) provides accurate volume aspiration and delivery of the sample. The linear relationship between the counted values of particles (i.e. beads of about 5.7 micrometer in diameter) and the known particle concentration shows the volume aspiration accuracy and thus the counting accuracy of our system. In addition, our direct absolute cell/particle counts remove the need to use expensive reference counting beads and provide consistent results between runs. With a high accuracy syringe pump controlling the injected sample volume and minimal cell loss in the fluidics, the flow cytometer achieves accurate direct cell counting without the need for expensive counting beads.

Figure 5:
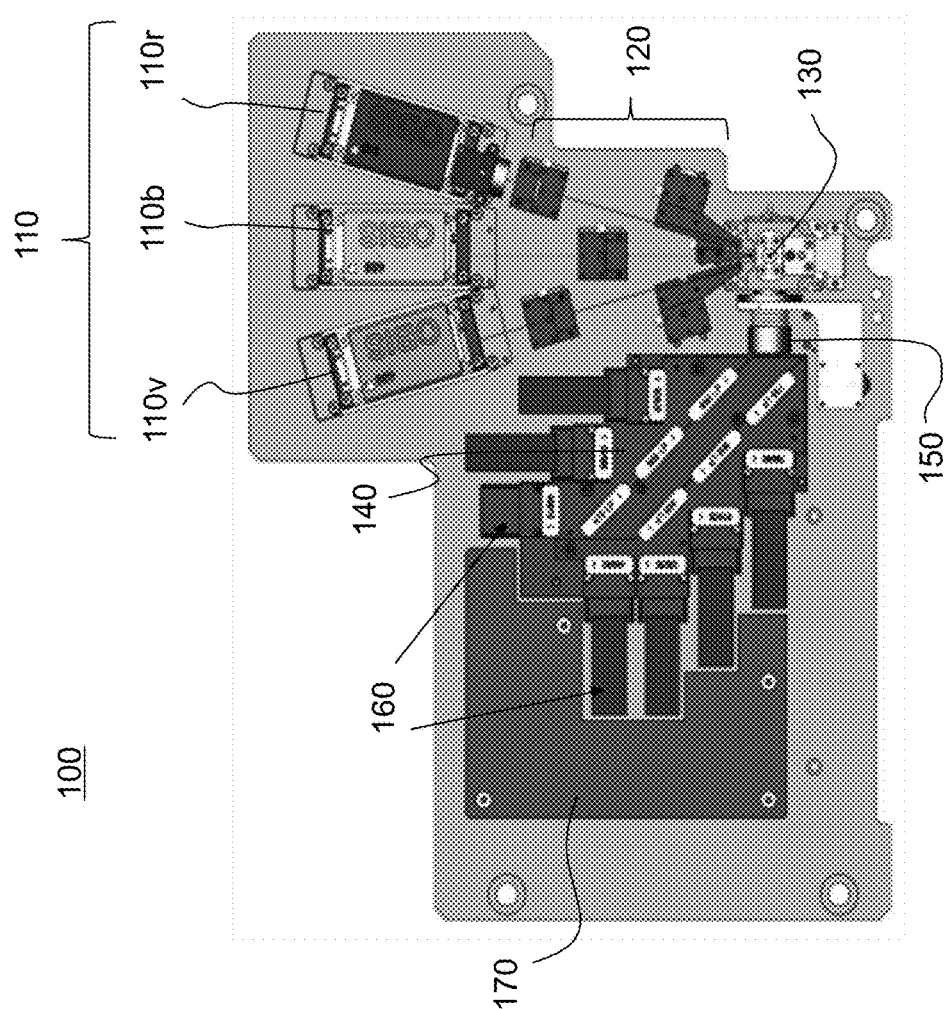
FIG. 5 is a top view of a representation showing an exemplary optical engine 100.

Turning to FIG. 5, a schematic providing an overview of our optical engine 100 is shown. The optical engine 100 includes from one to three lasers 110, and a set of beam shaping optics 120 for each laser 110 to independently shape and guide each excitation light source to the flow cell 130. Fluorescence is collected by collection optics 150, and separated into different channels by filtration optics 140. Detection of fluorescence is accomplished using a photo-multiplier tube (PMT) 160 for each channel. Also shown is a printed circuit board (PCB) housing 170, which houses the PCB including one or more microprocessors for operation of the flow cytometer 100 including automated system functions in response to commands from the developed control software, time monitoring of fluorescence detection and forward scatter detection to correlate fluorescence with a corresponding excitation laser 110. The syringe pump fluidics in fluidic connection with flow cell 130 is not shown here.

Although the optical engine may use a single laser 110, the optical engine 100 permits the flow cytometer 10 to perform multicolor flow cytometry analysis such as by measuring up to 15 parameters and 13 fluorescence signals from each fluorescently labeled cell. This has been achieved with three lasers 110 in FIG. 5. Conveniently, lasers 110 can be added, removed, or interchanged at least in part due to the individually assigned collection optics 150. An exemplary configuration for 13 color flow cytometry is shown in FIG. 5, including a first laser 110v emitting a wavelength of 405 nm (also referred to as violet laser), a second laser 110b emitting a wavelength of 488 nm (also referred to as blue laser), and third laser 110r emitting a wavelength of 640 nm (also referred to as a red laser). The skilled artisan will appreciate that the interchangeability of one or more lasers 110 permits the user to begin with a base flow cytometer system and add additional or different lasers 110 as experiments dictate such need. It is possible that during such interchange or exchange of one or more lasers, the corresponding beam shaping optics may be changed or adjusted to achieve the optimal delivery of the laser beam at the center of the flow cell.

FIG. 6 provides a simplified schematic of a top view showing beam shaping optics 120 for three exemplary optical paths (P1, P2, P3) for three laser beams from the three lasers (110v, 110b, 110r) of FIG. 3, where a first cylindrical lens 112v for the first laser 110v (e.g. 405 nm) focuses excitation light along an X-axis and a second cylindrical lens 114v focuses the excitation light from the first laser 110v along the Y-axis. Similarly, a first cylindrical lens 112b for a second laser 110b (e.g. 488 nm), focuses the excitation light along an X-axis and a second cylindrical lens 114b focuses the excitation light along a Y-axis. A set of two beam expanding lenses 111r expand excitation light from the third laser 110r (e.g. 640), followed by a first cylindrical lens 112r focusing the excitation light along an X-axis and a second cylindrical lens 114r for focusing the excitation light along a Y-axis. The light paths P1, P2, P3 from each laser 110 are focused to a single flow cell 130, through which cells are hydrodynamically focused into a narrow stream in the central region of a flowing sheath fluid.

Also shown is a half-ball lens 152 for collecting fluorescent light and side scatter light emitted from fluorescently labeled cells while travelling through the flow cell 130. An obscuration bar 190 is also shown, which blocks raw laser beam passing from P2 through the flow cell 130 and towards the forward scatter (FSC) focusing lens 192, which itself focuses FSC light from the second laser 110b (e.g. 488 nm) through a band-pass filter 194 (488/10 nm) for detection by a photodiode 196, which receives the FSC light and converts it to an electrical signal for data acquisition.

Figure 7:
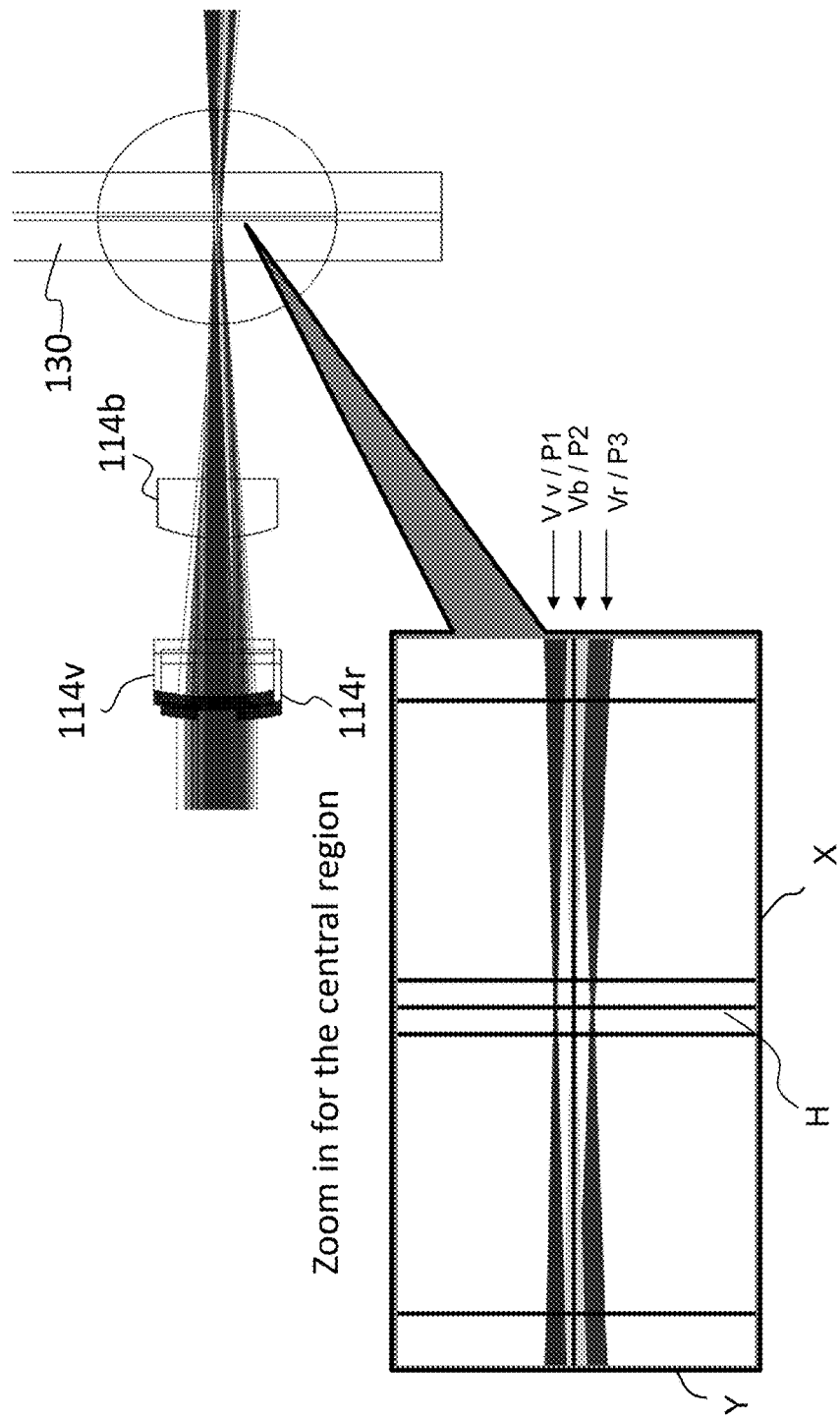
FIG. 7 is schematic depicting an enlarged view of the flow cell 130 showing a common focus position H for the three light paths P1-P3 and the different vertical focusing positions Vv, Vb, Vr of each path P1, P2, P3.

FIG. 7 is an enlarged schematic showing the three light paths (P1, P2, P3) directed through the corresponding second lens 114v, 114b, 114r converging at a common/same focusing position H (a centerline) along the flow cell 130 but focusing the laser beams at different vertical positions Vv, Vb, Vr along the flow cell 130. As a nonlimiting example, differential vertical focusing can be accomplished by adjusting the second cylindrical lens 114 to direct one beam above and one beam below a center beam. For example, the configuration shown in FIG. 5 vertically focuses Vv the first light path P1 from the first laser 110v upwards, by a given distance, (e.g. 80 μm) relative to the vertical focusing positioning Vb of the light path P2 via the second cylindrical lens 114b from the second laser 110b. This results in vertical focusing Vv of the first laser beam/light path P1 in the flow cell 130 vertically above the vertical focusing Vb of the second light path P2 by a same distance, (e.g. 80 μm). Similarly, adjusting the second cylindrical lens 114r for the third laser 110r downwards by a given distance (e.g. 80 μm) relative to the vertical position Vb of the second cylindrical lens 114b for the second laser 110b results in the vertical focusing Vr of the third laser beam P3 in the flow cell 130 vertically lower by the same distance (e.g. 80 μm) relative to the second laser beam P2. The skilled artisan will appreciate that while this separation is depicted 80 μm apart, separations more or less than these could be performed. In some embodiments the beams P1-P3 are separated from neighboring beams P1-P3 by 70 μm. In other embodiments, separation is 75 μm, 85 μm, 90 μm, 100 μm, 125 μm, 150 μm, 175 μm, or 200 μm. Furthermore, adjusting the Z-axis positions of the three above-mentioned second cylindrical lenses 114v, 114b, 114r allows the three laser beam's Z-axis focal points coincide with the center line in the flow cell 130, thus leading to the coincidence of laser beams' Z-axis focal points within the focused sample narrow stream. By focusing at different vertical positions Vv, Vb, Vr along a flow cell 130, a comparison can be made between time of fluorescence signal and time of forward scatter signal to determine the identity of an excitation laser that induced a particular detected fluorescence.

In an alternative method, laser sources may be modulated at different frequencies. Demodulation of fluorescence-converted electrical signals can be performed to determine the laser source for a given fluorescent signal at a particular time point. Previous patent application titled "System and Method for Detecting Multiple-Excitation Induced Light in a Flow Channel", having a U.S. patent application Ser. No. 13/657,845, describes the apparatus, method and techniques for such modulation and demodulation of laser beams in a flow cytometer application. This application U.S. Ser. No.

13/657,845 is incorporated by reference in its entirety. The identification of fluorescence signals with corresponding laser excitation can be achieved through either forward-scatter-coincidence method or laser-modulation and fluorescence-demodulation method, or combination of both methods. This way, detection at each detector can be performed so that detected, filtered fluorescent signals are assigned to corresponding lasers, which are focused at different vertical positions along the flow cell.

Referring collectively to FIGS. 5-7, there are unique advantages for independently controlling three separate optical paths P1, P2, P3 from three lasers 110v, 110b, 110r. First, it is straightforward to separately adjust the alignment of each focused beam along the X-axis to the hydrodynamically-focused sample stream, by adjusting the X-axis position of first cylindrical lens 112 using a horizontal adjuster 113a. This can be used to eliminate interference between different laser beams and between different optical paths P1, P2, P3, thus allowing each laser beam to be adjusted to optimal alignment.

Secondly, one can independently adjust the Z-axis positions of the second cylindrical lens 114 for each laser beam, ensuring the coincidence or alignment of the focal plane for the Y-axis beam with the hydrodynamically-focused fluid stream in the flow cell 130. Again, there is no interference between different laser beams and between different optical paths P1, P2, P3, thus allowing each laser beam to be adjusted to the optimal alignment with the fluidics.

Thirdly, one can readily adjust and control the separation distance along the Y-axis between three different beams in the flow cell 130, by simply adjusting and moving the height of the second cylindrical lens 114 along the Y-axis for each laser beam using a height adjuster 113b. With such an approach, one could adjust the beam separation distance continuously over a relatively-large range.

Fourthly, by providing separate beam shaping and beam guidance optics for each laser independently of the others, one could choose or use lasers 110 having the same or different raw beam diameters, since for each channel different cylindrical lenses 112, 114 could be used with different focal lengths to accommodate the difference in the raw beam diameters.

Fifthly, such an optical illumination design would allow easy configuration and possible upgrade of the laser illumination sources. For example, one could start with a system having a single laser 110 as excitation source. When there is a need for providing additional laser 110 sources of different wavelengths, the new laser(s) 110, together with its (their) corresponding beam shaping and guidance optical components 120, could be readily added to the system, without affecting the existing laser 110 and its beam shaping optics 120. These unique advantages would allow optimal alignment and focus of each laser beam in the flow cell 130, overcoming the limitations compared to other light illumination designs where different lasers share the same optical path for beam shaping and beam separation, and focus and alignment for different lasers need to be compromised.

Forward light scatter (also referred to as forward scatter or low angle scatter) refers to the measurement in flow cytometry that involves light refracted forward due to the passing of a cell through a laser beam and is roughly proportional to the diameter of the cell. When no cell is passing through the path of the laser beam the beam passes uninterrupted through the flow cell 130 and is blocked by an obscuration bar 190 so that no light from the laser beam itself would arrive in the detector. However, when a cell passes through the flow cell 130, light is refracted in all directions. The light refracted in the forward direction misses the obscuration bar 190 to reach the forward scatter detector 162. To this end, different obscuration bars were developed and tested.

FIGS. 8A-B show plots of a light intensity distribution to determine the effect of a laser beam at FSC obscuration bar 190 position. FIG. 8A shows results without a hydrodynamically (HD) focused core, i.e. the flow cell is filled with a homogeneous sheath fluid. In this instance, the laser beam is of a vertical, elliptical shape and can be blocked with a vertical bar. Yet, as shown in FIG. 8B when hydrodynamic core is resulted (in this instance a 17 μm focusing core) when a sample fluid having a refractive index higher than that of the sheath fluid is hydrodynamically focused into the central core region surrounded by the sheath fluid, one sees a biconvex lens effect with a horizontally-expanded beam. This demonstrates the need for an improved FSC obscuration bar to match and block this horizontally expanded beam.

Figure 9:
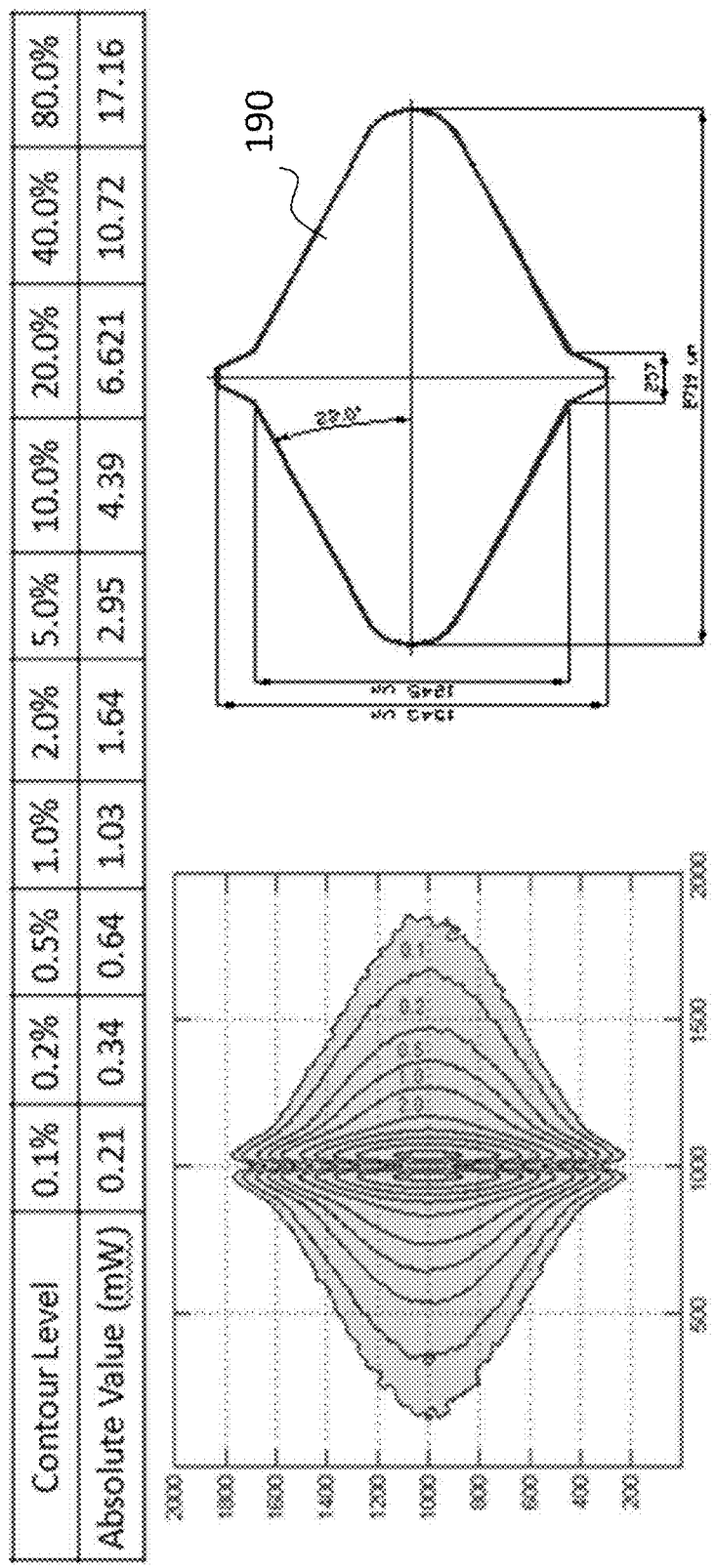
FIG. 9 is a schematic showing the shape of an obscuration bar (right panel) compared to the contouring of a light intensity distribution for the case where a laser beam is passing through a flow channel with a hydrodynamically focused core as shown in FIG. 8B and the resulting laser power for the regions outside each contoured line for a 20 mW laser illumination.
Figure 10:
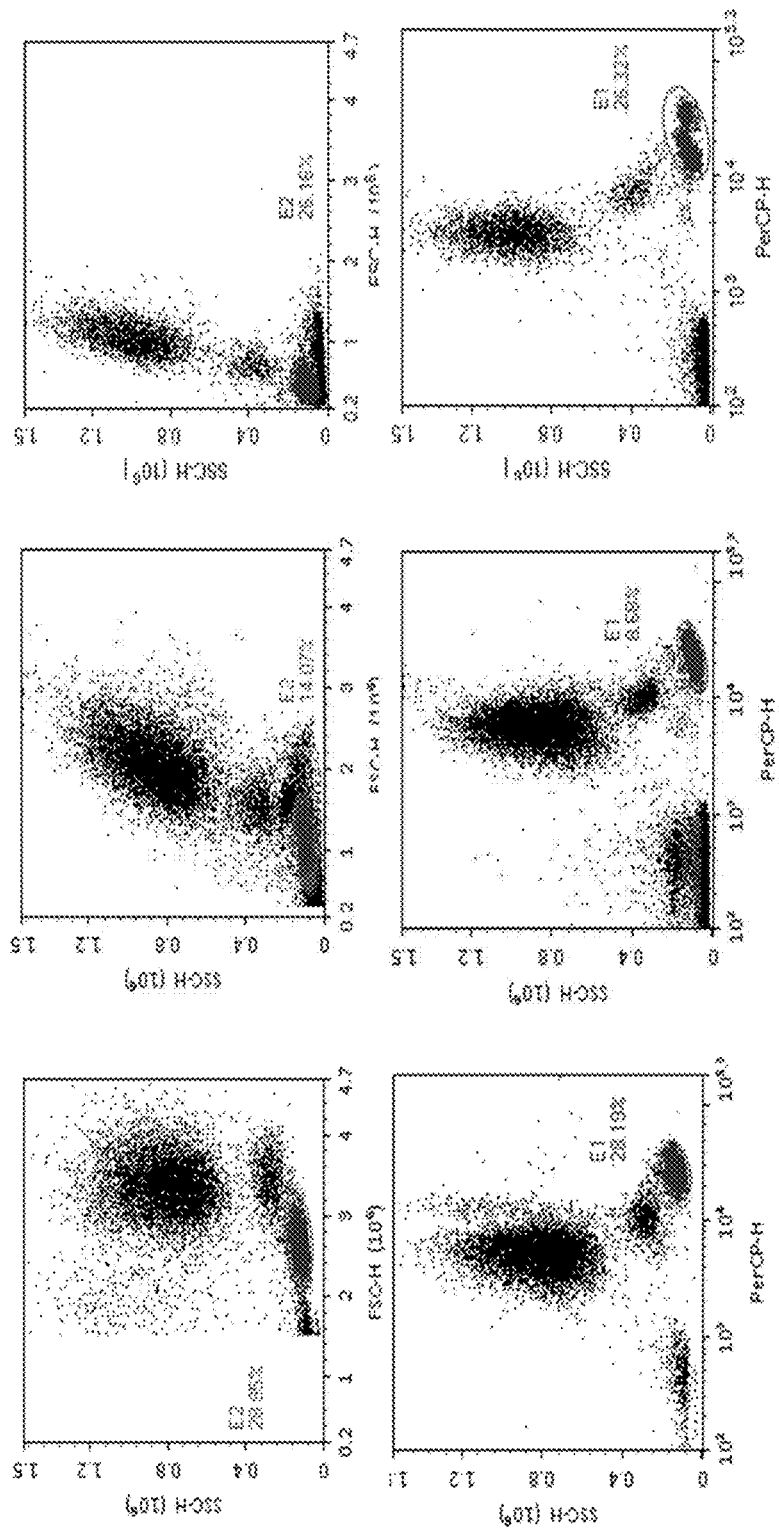
FIG. 10 is a series of plots showing the varying ability to effectively identify lymphocytes (E2 populations) using FSC vs SSC plots using either a diamond obscuration bar (panel A); a vertical obscuration bar (panel B); or a horizontal obscuration bar (panel C). For comparison purposes, SSC vs CD45 plot was used as control for each panel. As shown in this example, lymphocyte E2 populations could be separated out from debris or other cellular populations when diamond bars were used (panel A).

As described above, examination of FIG. 8B reveals that the light intensity distribution due to the convex effect (on the vertical laser beam showing in FIG. 8A) of hydrodynamic core surrounded by the sheath fluid demonstrated that the laser beam is horizontally expanded at FSC obscuration bar 190 position. To block such a light distribution, one approach is to design the obscuration bar having a rectangular shape, with a longer horizontal dimension that its vertical dimension. Thus, preferably, the obscuration bar for blocking the incident laser beam has a rectangular shape with its horizontal size being the same as or longer than its vertical size. FIG. 9 depicts an overview of our technical approach to form a new FSC obscuration bar 190. The obscuration bar 190 can be used with our system or others. To determine and test different forms of our obscuration bar 190, we performed a contour plot of laser beam energy distribution at the FSC bar position and determined the amount of laser energy outside of the contour lines to assess efficiency of different configurations. Pictorially we label contour levels of 0.1%, 0.2%, 0.5%, 1.0% and 2.0% in the contour plot of FIG. 9 and provide data in the Table above the graphs for a number of different contour levels, which reflects the total laser energy outside this contour line. For example, our calculations show that the energy outside of a 0.2% contour line is 0.34 mW and the energy outside of 0.1% contour line is 0.21 mW. To block about 99% of the beam, we can design a diamond-shaped obscuration bar 190, based on 0.1% contour line, leaving about 0.2 mW laser beam unblocked. As such, in a preferred embodiment the obscuration bar 190 follows the 0.1% contour level; however, an obscuration bar 190 that follows the 0.2%, 0.5%, 1.0%, 2.0% could be used with less than optimum results. Also shown in FIG. 9 are the dimensions of our preferred diamond-shaped, 0.1% obscuration bar 190. FIG. 10 is a series of plots comparing FSC signals when using different obscuration bars, namely our diamond-shaped bar (panel A), a vertical bar (panel B), and a horizontal bar (panel C). Experimentally, a blood sample was lysed but not washed. As shown in panel B, the vertical bar was not able to allow clear separation of lymphocytes from other WBCs. The lymphocyte percentage is approximately 8.7% at CD45-PerCP vs SSC plot yet a gating on FSC vs SSC showed a much higher percentage (about 14%). Note the E1 population is lymphocytes from a CD45 vs SSC plot for comparison. E2 is a population gated from FSC vs SSC plot. For the vertical bar situation (panel B), whilst the lymphocytes appear to be separated from other WBCs, they could not be readily separated from debris. Our diamond-shaped bar (panel A) provided best separation of populations.

While forward scatter is detected generally along the propagation path of the laser, side scatter is collected orthogonal to the incident laser beam. Side-scattered light is proportional to the overall size of the cell but is also affected by cell characteristics like internal complexity or granularity of a cell and the smoothness of a cell's membrane. As a general rule of thumb a rough cell or a cell with internal complexity would result in a relatively high side scatter. The invention also provides for the detection of side scatter as will be more evident in FIG. 11.

Figure 11:
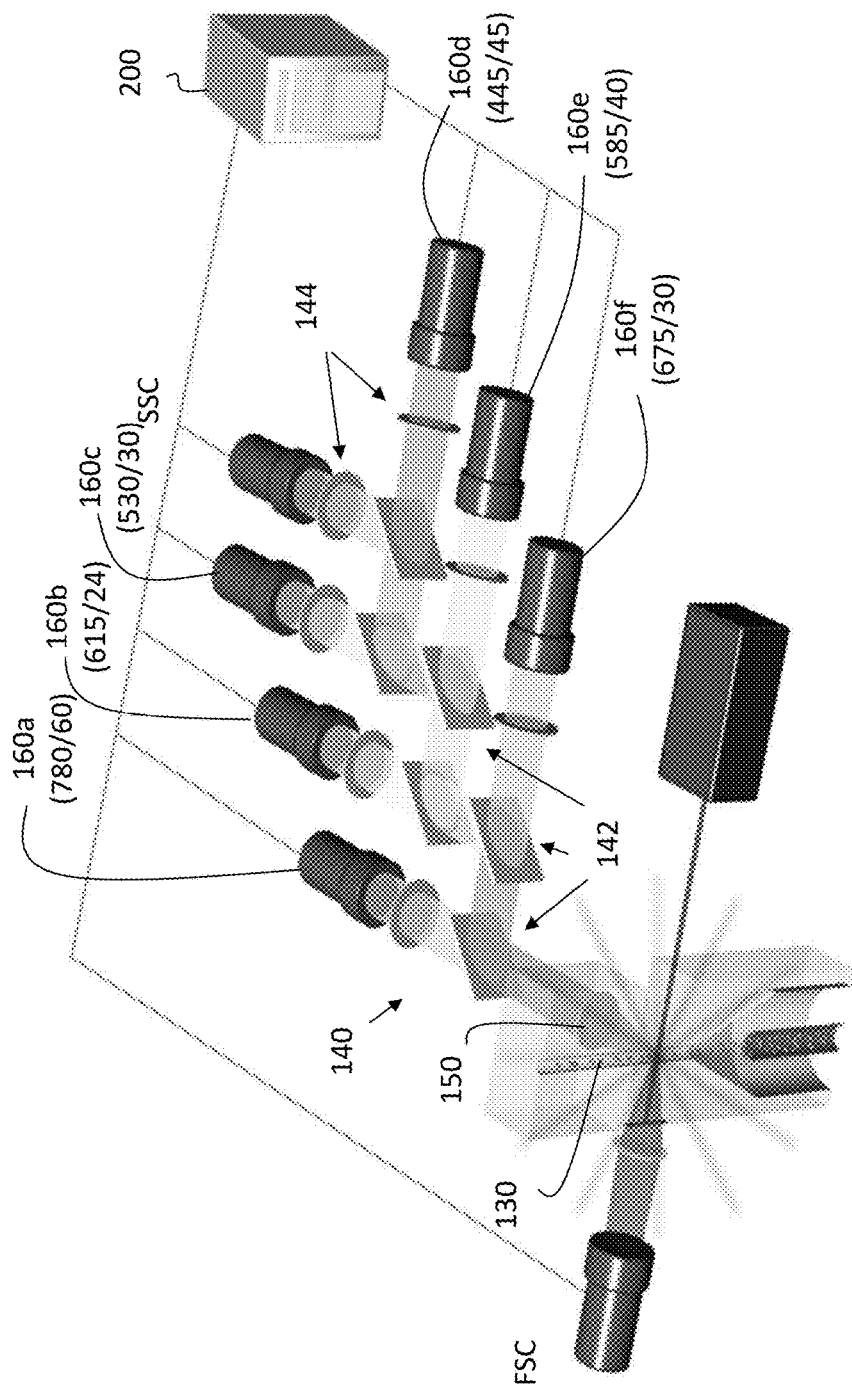
FIG. 11 is a schematic showing the splitting of collected light from a flow channel in a flow cell into six different fluorescent wavelength ranges plus one side scatter channel (SSC). Using apparatus and methods in the present invention, the six fluorescent wavelength ranges could correspond to 13 fluorescent color channels.

Flow cytometry conventionally includes the labeling of cells with one or more fluorophores. This is typically performed by adding a fluorescently labeled reagent, such as a fluorescently labeled antibody against a surface marker, to a suspension of cells, then washing away unbound reagent. Fluorophores present on or in the cell as it passes through the laser beam adds to the cumulative signal from the cell. Such reagents are well known in the art and available from many suppliers. Both side scatter and fluorescence are collected through collection optics positioned generally orthogonal to the laser beam path then filtered and reflected into a different channels using dichroic mirrors. Dichroic mirrors permit passage of a certain wavelength ranges and reflect the remaining wavelengths. An overview of this is shown in FIG. 11, where fluorescence and SSC signals from a flow cell 130 are collected using collection optics 150 then split into different detection channels with filtering optics 140, primarily comprised of long pass and/or short pass dichroic mirrors 142 and bandpass filters 144. Shown are six PMTs (160*a-f*) for the detection of the following six fluorescent wavelengths: 780/60 nm (160*a*), 615/24 nm (160*b*), 530/30 nm (160*c*), 445/45 nm (106*d*), 585/40 nm or 572/28 nm (160*e*), 675/30 nm (106*f*). The PMTs 160 then electrically communicate with a computer 200 for data collection, which may also include analog to digital conversion. Using the channel configuration shown in FIG. 11, TABLE 1 provides a nonlimiting listing of compatible fluorophores for conducting 13 color flow cytometry analysis, when each PMT detector could be used to derive fluorescence signals from different lasers.

Further, by focusing excitation laser beams at distinct vertical positions along the flow cell 130, defining optical paths for each of the vertical positions for measurement, providing detectors with sufficient sensitivity, and determining differences between time of fluorescence signal and forward scatter signal of a same cell or particle, measurement of 13 fluorescent colors of a single cell has been achieved using three lasers with 6 PMT configuration shown in FIG. 11. TABLE 1 illustrated how each PMT channel is shared among different fluorescence channels due to different laser excitations. For example, PMT channel at 530/30 nm is shared for detection of fluorescent signals with wavelength ranges from 515 to 545 nm, excited by both violet laser and blue laser. In another example, PMT channel at 675/30 nm is shared for detection of fluorescent signal with wavelength ranges from 660 to 690 nm, excited by all three lasers, i.e. violet laser, blue laser and red laser.

Figure 12:
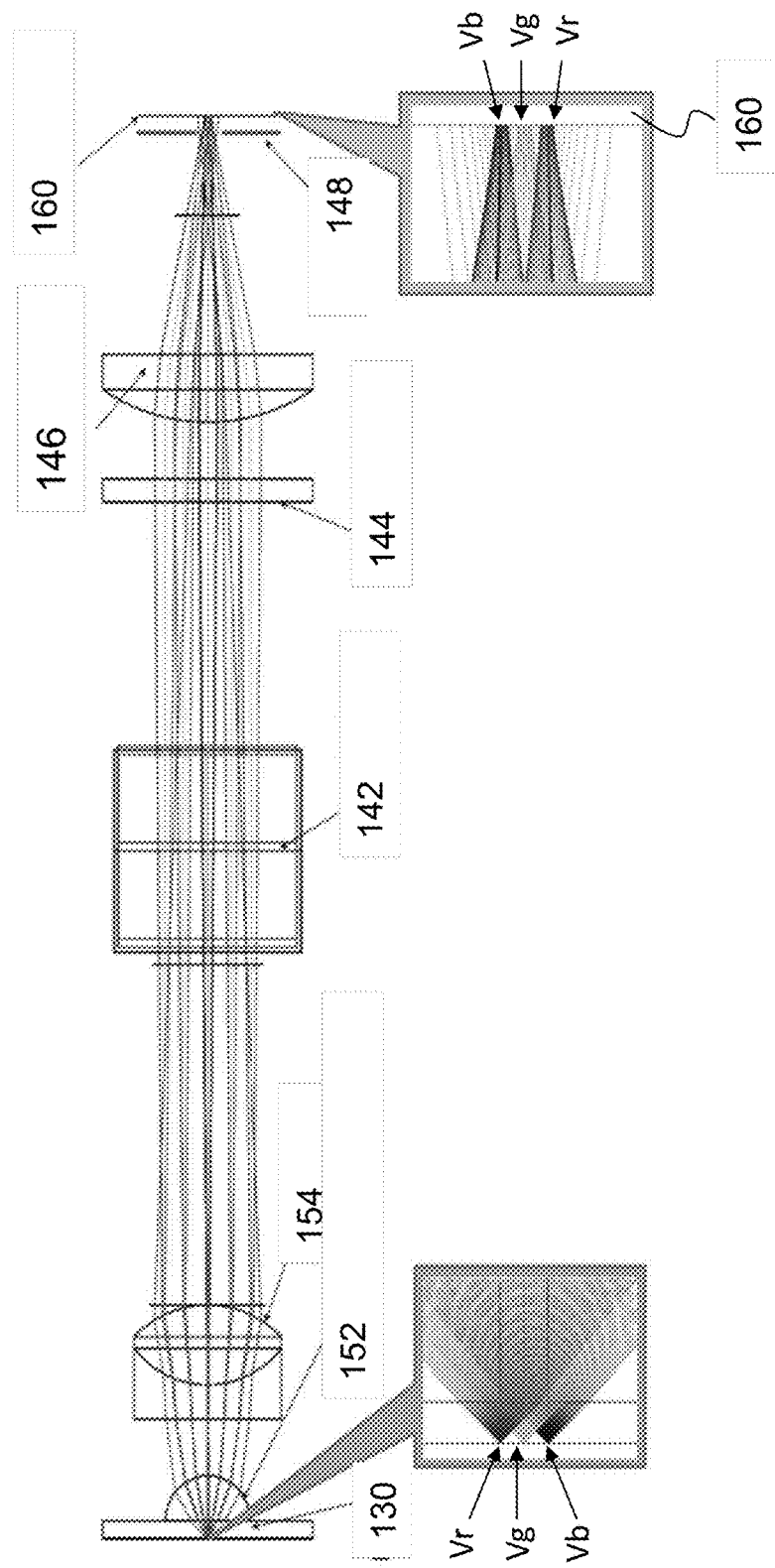
FIG. 12 is a schematic showing that fluorescent light from three different vertical positions (Vr, Vg, Vb) from a same flow cell 130 is collected by collection optics and travels through light splitting modules 142 to be filtered by a band-pass filter 144 and focused by a lens 146 to be detected at a detector 160.

A more detailed schematic of the collection and measurement of spatially distinct positions along a single channel is shown in FIG. 12. Fluorescence from three distinct vertical positions (Vv, Vg, Vr) along a flow cell 130 is collected using a high refractive index half ball lens 152 (in this example n=2). The optical path of each proceeds through an achromatic doublet lens 154 (in this example N.A.=1.0) for collimating fluorescent light and filtered through one or more dichroic mirrors 142. As already eluded to, the half-ball lens 152 is preferably made of high refractive index materials. Such a choice is for maximize the Numerical Aperture (N.A.) and for reducing the overall diameter/size of the fluorescent light beam following the half-ball lens 152. This reduced beam diameter also permits a smaller diameter for the doublet lens 154, making the design and manufacturing of such a doublet lens 154 somewhat less-difficult. It has been found that the combination of high refractive index half-ball lens 152 and doublet lens 154 results in a high numerical-aperture objective for collecting fluorescent light efficiently. Such a design not only results in a high collection efficiency but also leads to a reduced cost for design and manufacturing of such objectives. The optical path then proceeds through a bandpass filter 144, a focusing lens 146, a pinhole 148 and finally to the PMT 160. An

TABLE 1

|  | Excitation | 445/45 | 530/30 | 585/40 | 615/24 | 675/30 | 780/60 |
|---|---|---|---|---|---|---|---|
| Pacific Blue | 405 nm | X | | | | | |
| BRILLIANT VIOLET 421 | 405 nm | X | | | | | |
| DAPI | 405 nm | X | | | | | |
| AmCyan | 405 nm | | X | | | | |
| PACIFIC ORANGE | 405 nm | | | X | | | |
| QDOT 605 | 405 nm | | | | X | | |
| QDOT 655 | 405 nm | | | | | X | |
| QDOT 800 | 405 nm | | | | | | X |
| Fluoroscein | 488 nm | | X | | | | |
| FITC | 488 nm | | X | | | | |
| ALEXA FLUOR 488 | 488 nm | | X | | | | |
| GFP | 488 nm | | X | | | | |
| PI | 488 nm | | | X | X | | |
| PE | 488 nm | | | X | | | |
| PE-CY 5 | 488 nm | | | X | | | |
| PE-ALEXA FLUOR 610 | 488 nm | | | | X | | |
| PE-Texas Red | 488 nm | | | | X | | |
| PERCP | 488 nm | | | | | X | |
| 7-AAD | 488 nm | | | | | X | |
| PE-CY7 | 488 nm | | | | | | X |
| APC | 640 nm | | | | | X | |
| ALEXA FLUOR 647 | 640 nm | | | | | X | |
| APC-CY 7 | 640 nm | | | | | | X |
| ALEXA FLU0R 700 | 640 nm | | | | | | X | enlarged PMT 160 schematic is also shown in the figure insert showing the spatial distinction from each of the vertical positions Vv, Vg, Vr from the flow cell 130. To assess the sensitivity of the system, light collection efficiency was determined across the PMTs 160 in ZEMAX software and under an exemplary condition, it was found that about 70% efficiency of light collection was achieved at the last PMT 160 along the optical path, which is considered high efficiency of light collection.

Figure 13A:
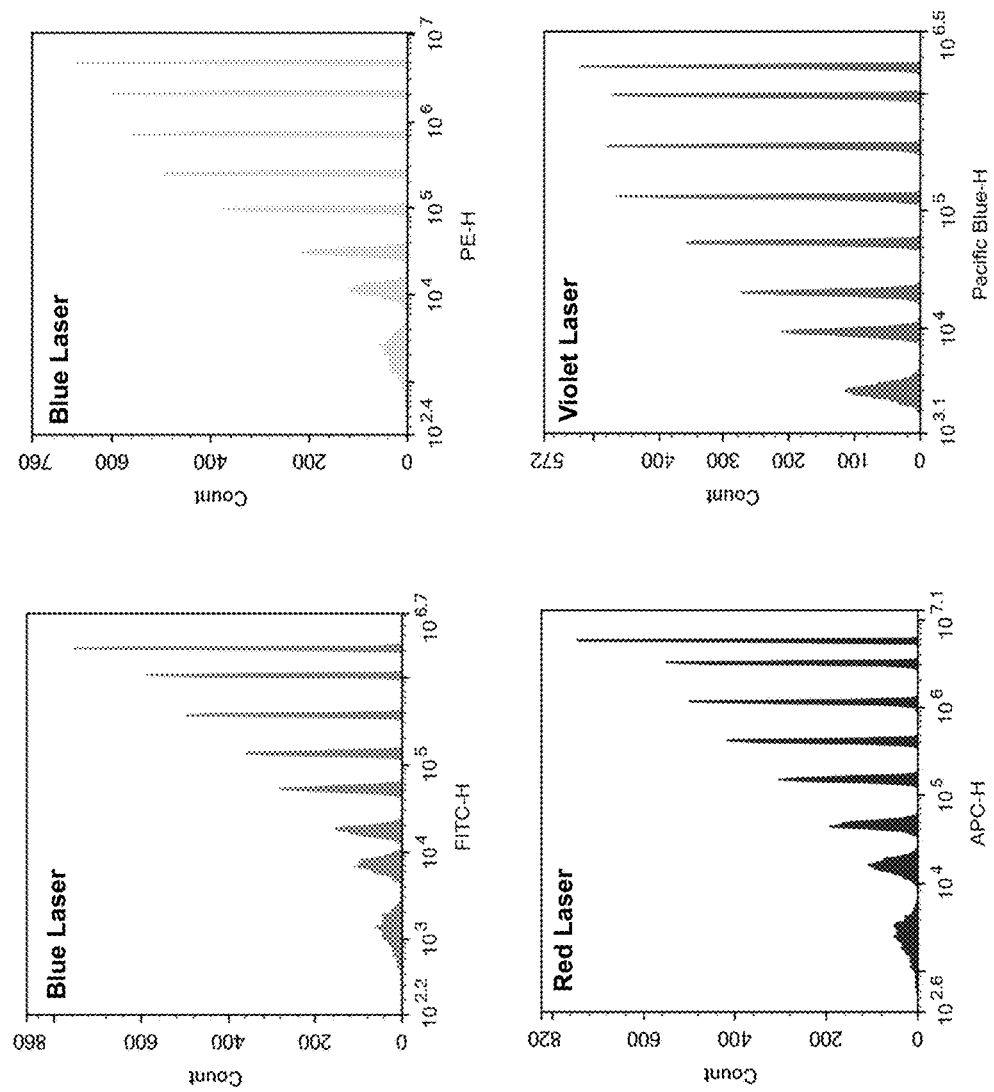
FIG. 13A shows a series of histogram plots showing that our cytometer could clearly separate beads with eight distinguishable fluorescence intensities on various fluorescent detection channels.
Figure 13B:
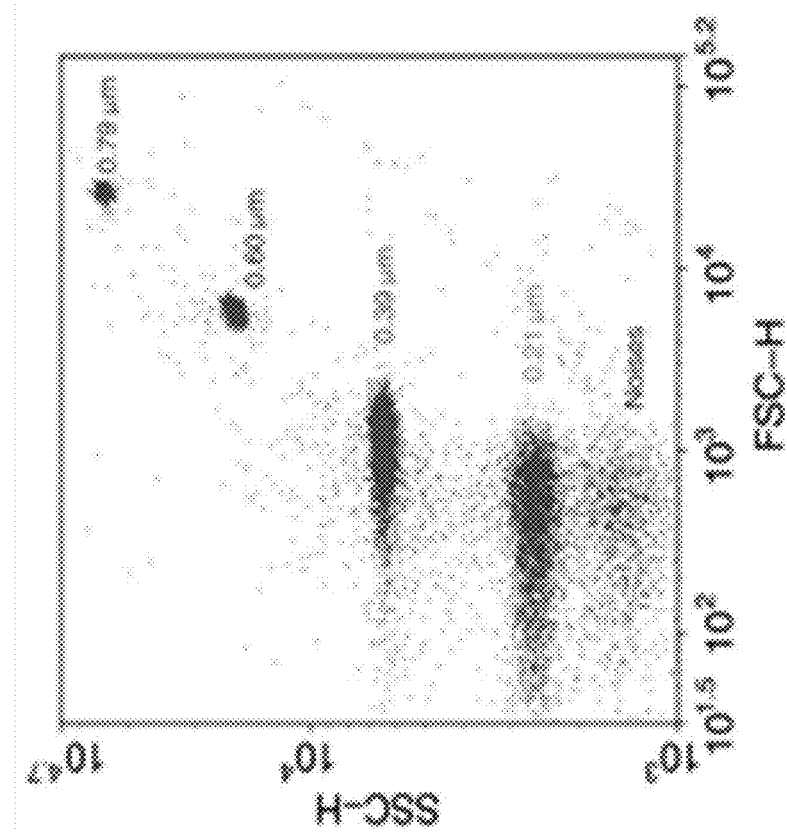
FIG. 13B is a forward scatter (FSC) vs. side scatter (SSC) plot showing the visualization of different sized beads having sizes of 0.21 μm, 0.39 μm, 0.60 μm, and 0.79 μm.

Resolution and sensitivity were further tested at different fluorescence channels to ensure reliability across the fluorescence channels. Exemplary results are shown in FIGS. 13A-B, where FIG. 13A shows that each of 8 peaks bead populations (i.e. consisting of 8 different fluorescence intensities was clearly separated from each other when analyzed at fluorescent detection channels of FITC (530/30 nm, excited by blue 488 nm laser), PE (585/40 nm, excited by blue 488 nm laser), APC (675/25 nm, excited by red 640 nm laser), or PACIFIC BLUE (445/40 nm, excited by violet 405 nm laser). As shown in FIG. 13B, beads of sizes 0.2 µm, 0.4 µm, 0.6 µm were also clearly observed using forward scatter and side scatter.

Control and communication to the flow cytometer for setup and data acquisition is performed using a computer communicatively coupled to the flow cytometer. Accordingly, flow cytometry software for loading in a computer has also been developed. The flow cytometry software preferably includes data acquisition features and data analysis features. As known in the flow cytometry arts, data acquisition involves the collection and storing of data from an experiment. This may also include set up features for acquiring data, such as compensation adjustment, defining the number of cells to be counted within a particular gated population, setting a sample flow rate, and the other experiment controls encountered in the flow cytometry arts. Data analysis features may include plotting cell subpopulations across one or more fluorescent colors, determining absolute counts for particular cell subpopulations, determining relative percentages of particular subpopulations, cell cycle analysis, as well as other data analysis features found in flow cytometry programs. To this end, the software provides versatile, user friendly and intuitive plotting and gating tools and its statistical tools provide exceptional statistical data analysis capabilities. In preferred embodiments, all acquisition parameters, experiment and sample files, along with plots are visible and accessible in one window area.

In some embodiments, a data collection process can include calculating and processing fluorescence signals for the same detector to separate them out into different fluorescence channels from different lasers (at different vertical positions); generating a graphical user interface (GUI) that displays two-dimensional plots with one parameter versus another one (e.g. FSC vs. SSC, FSC vs. a fluorescence signal, or one fluorescence signal vs. another fluorescent channel), wherein the GUI further comprises compensation scroll bars adjacent to the comparison plots to adjust compensation of spectral overlap between one or more channel; collecting data from each light scatter channel and from each fluorescence channel; and saving the data into a data file. The software also preferably includes a gating function that permits the user to select a subpopulation from one of the histogram plots or one of the 2-D plots and generate another plot (which could either be a one-parameter histogram plot or be a two-parameter 2-D plots for the selected subpopulation. This "gating" and further analysis of "gated populations" can be repeated.

Figure 14:
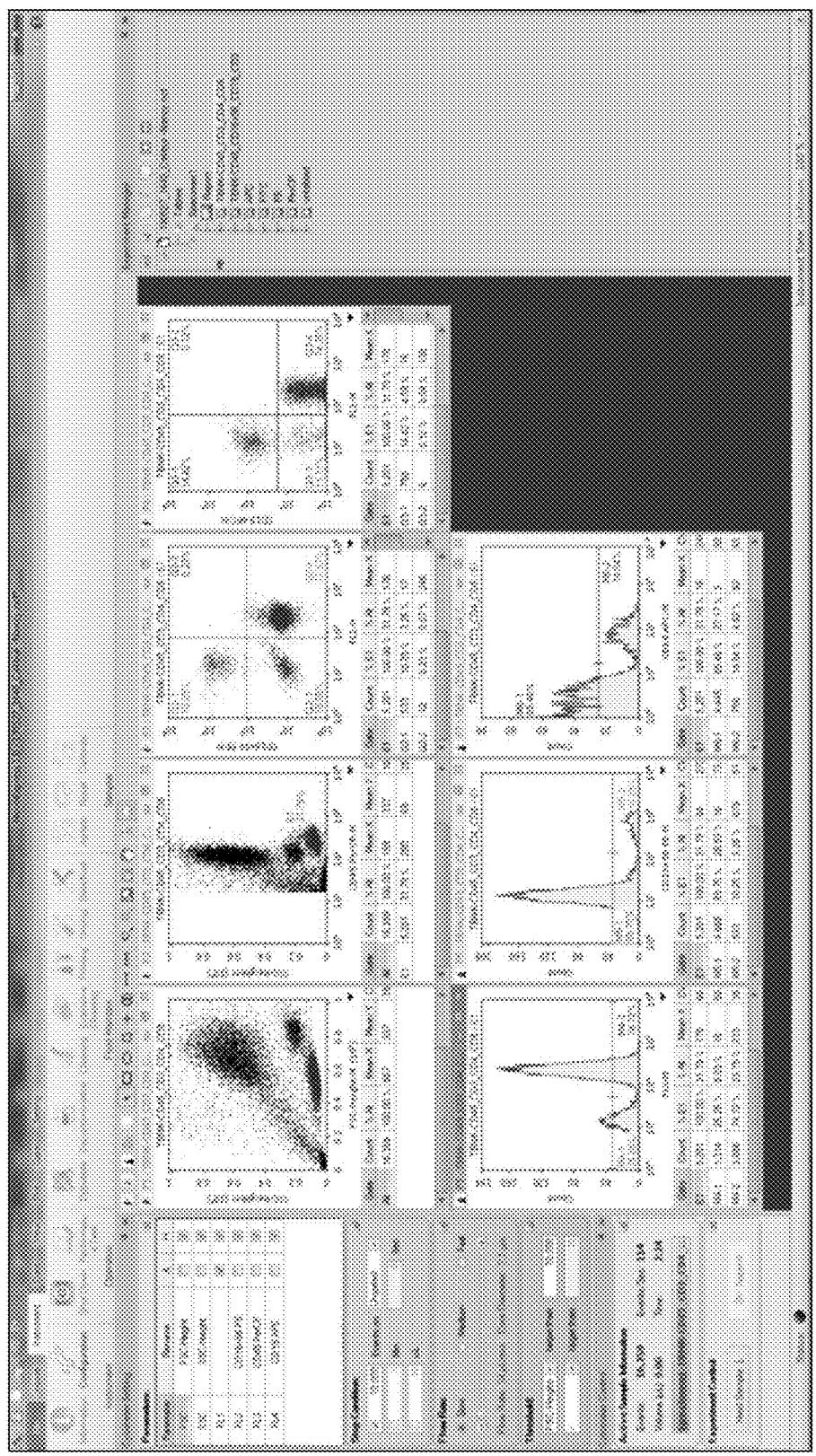
FIG. 14 is a screen shot from the graphical user interface (GUI) of the software system when loaded and running on a computer.

An exemplary GUI screenshot is shown in FIG. 14, which shows an experiment manager screen overviewing the experiment file with numerous data plots shown in a single window. The software can provide automatic laboratory report, showing the histogram graphs, or 2-D plots, the gating and other statistics for the data within the gates, etc.

Figure 15:
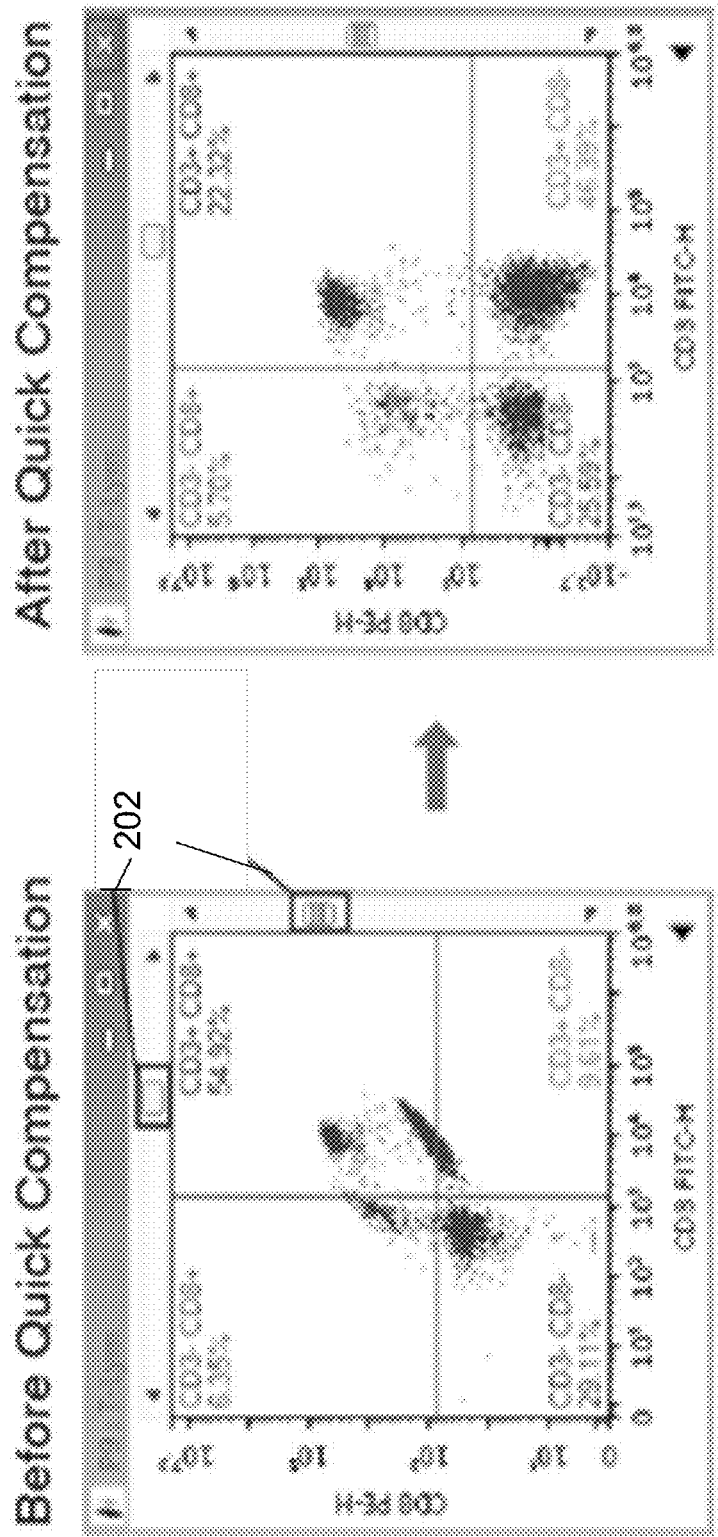
FIG. 15 is a screen shot of plots shown before and after adjusting compensation via movable scroll bars displayed on the screen.
Figure 16:
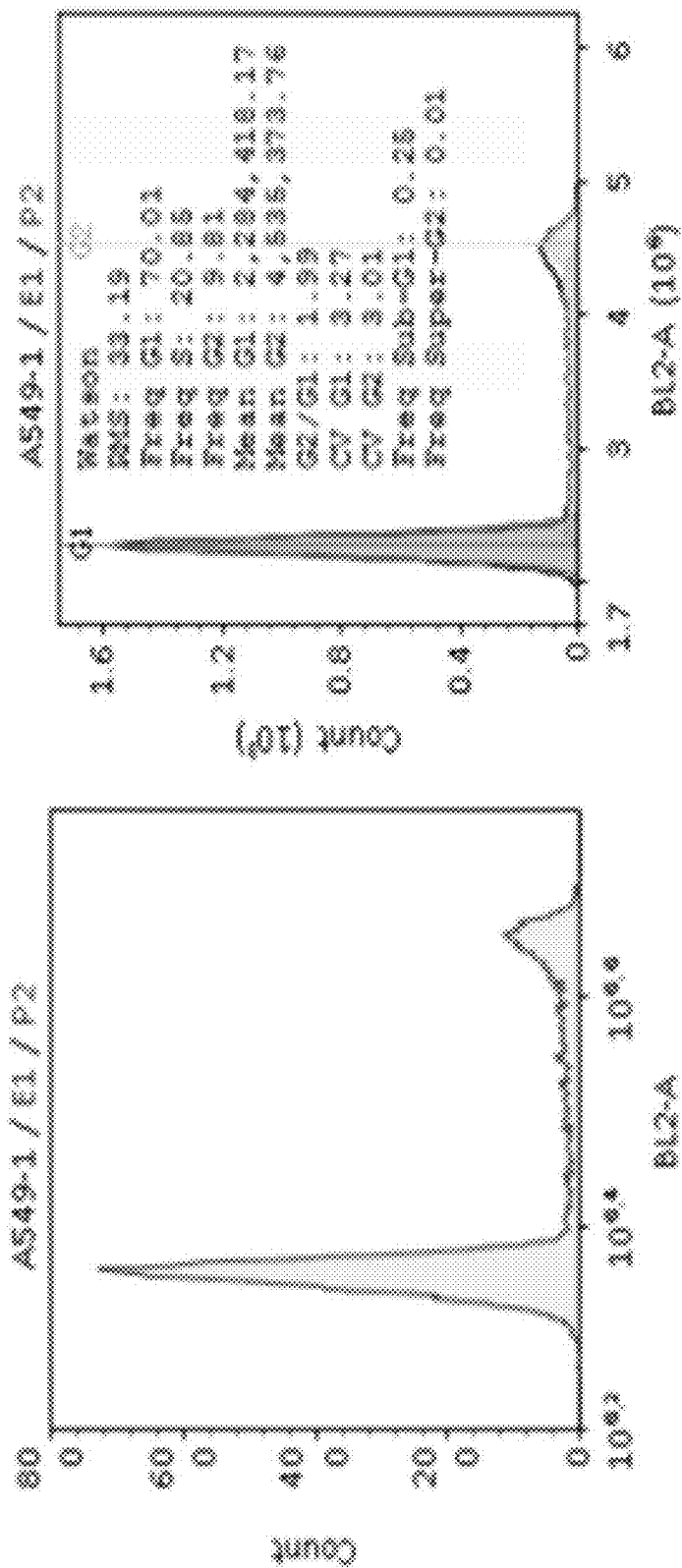
FIG. 16 is a series of histogram plots from an experiment showing the cell cycle distribution (reflecting DNA contents as measured on 585/40 nm channel, excited by a blue laser) for A549 cells.
Figure 17:
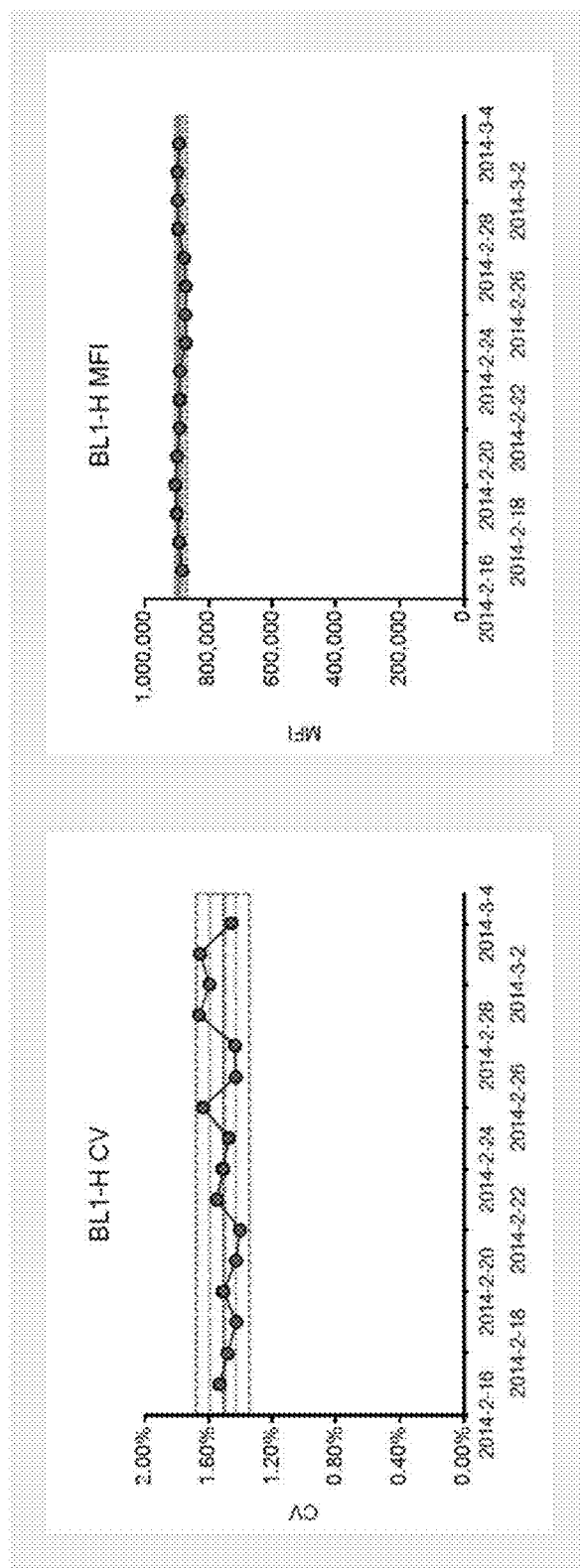
FIG. 17 is a series of graphs showing Levy-Jennings plot of detected Mean Fluorescence Intensity (MFI) and Coefficient of Variation (CV) of the 530/30 detection channel off the blue laser (BL1).
Figure 18:
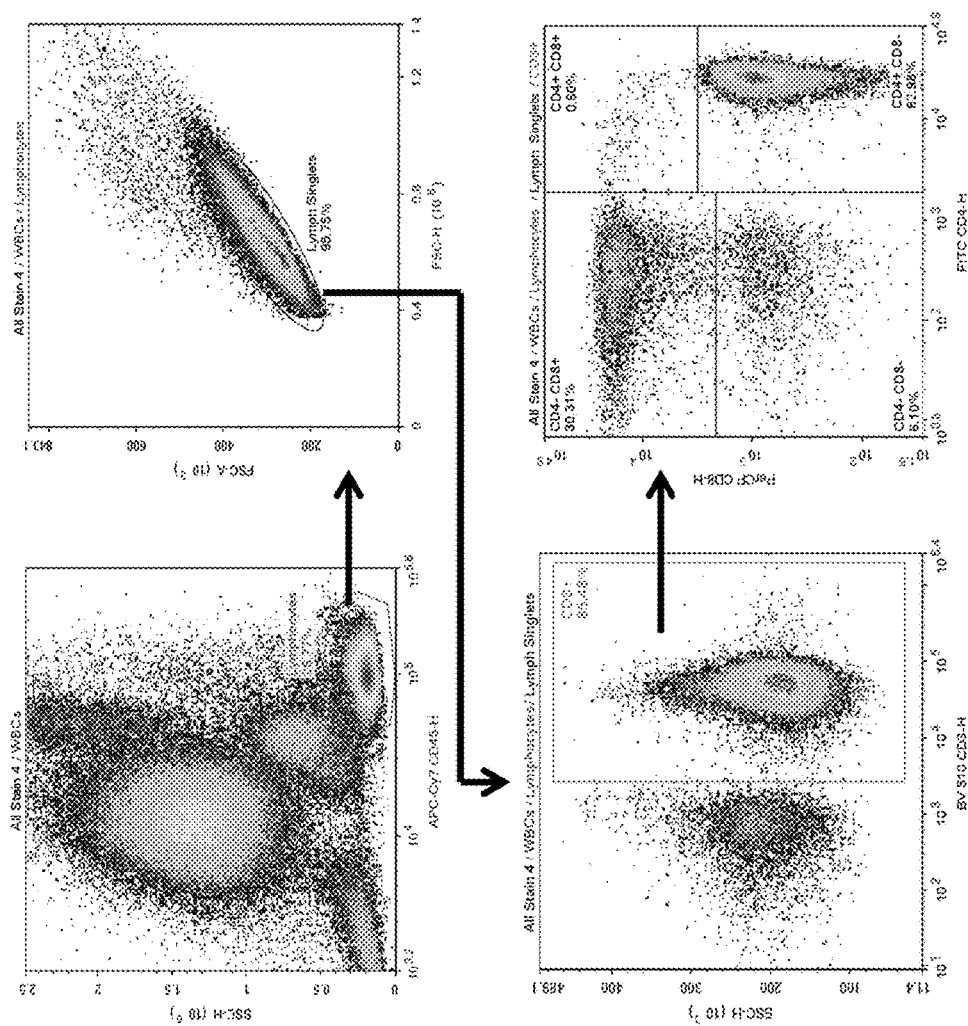
FIG. 18 is a series of plots showing the gating of lymphocytes using SSC vs. CD45, identifying CD3+ cells and further identification of cells by FITC/CD4 vs PerCP/CD8 plots.
Figure 19:
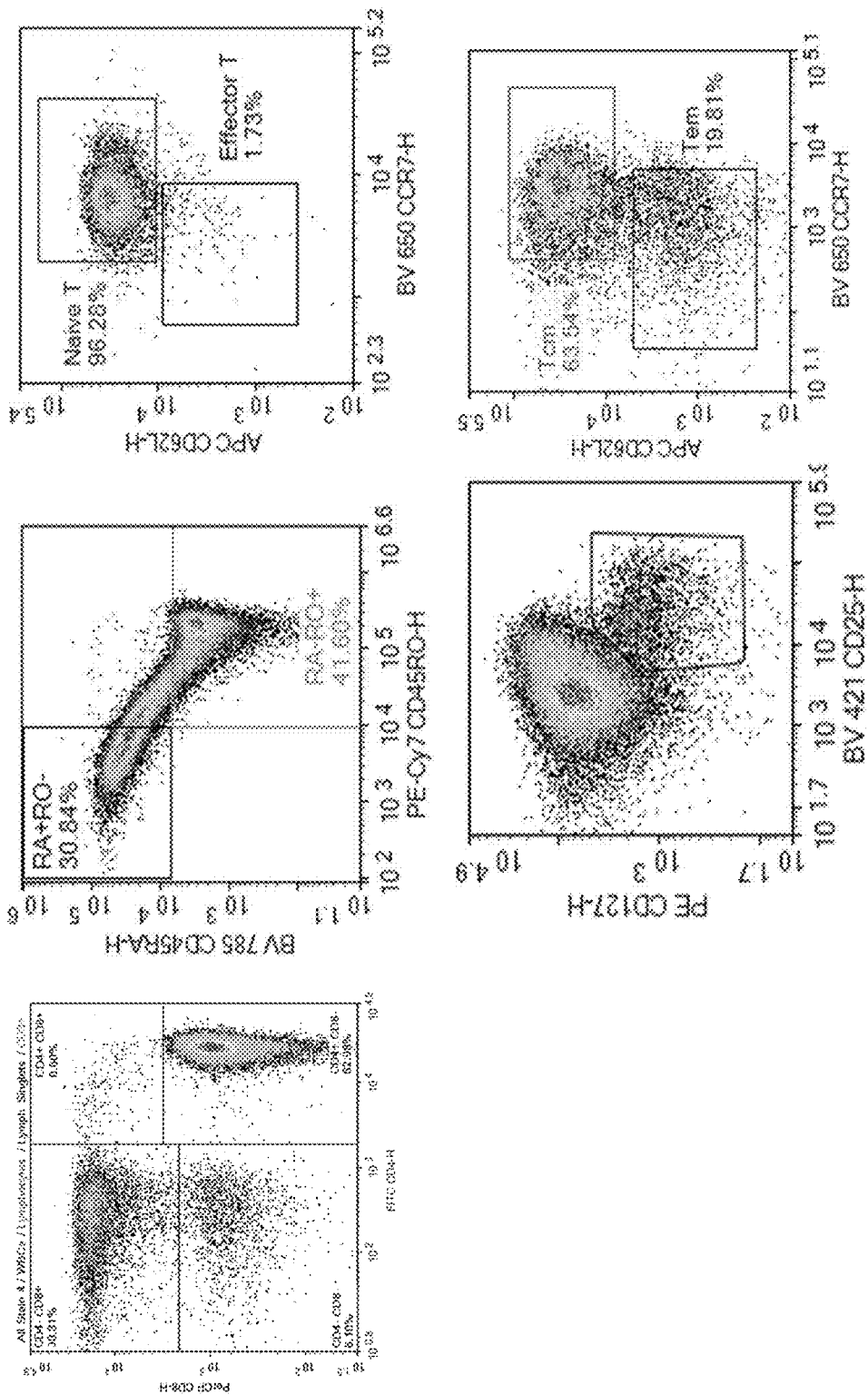
FIG. 19 is a series of plots where either CD4+/CD8− cells were further analyzed in a CD45RA vs. CD45RO plot. Furthermore, the populations of CD45RA+/CD45RO− and CD45RA−/CD45RO+ cells were analyzed in CCR7 vs. CD62L plots.
Figure 20:
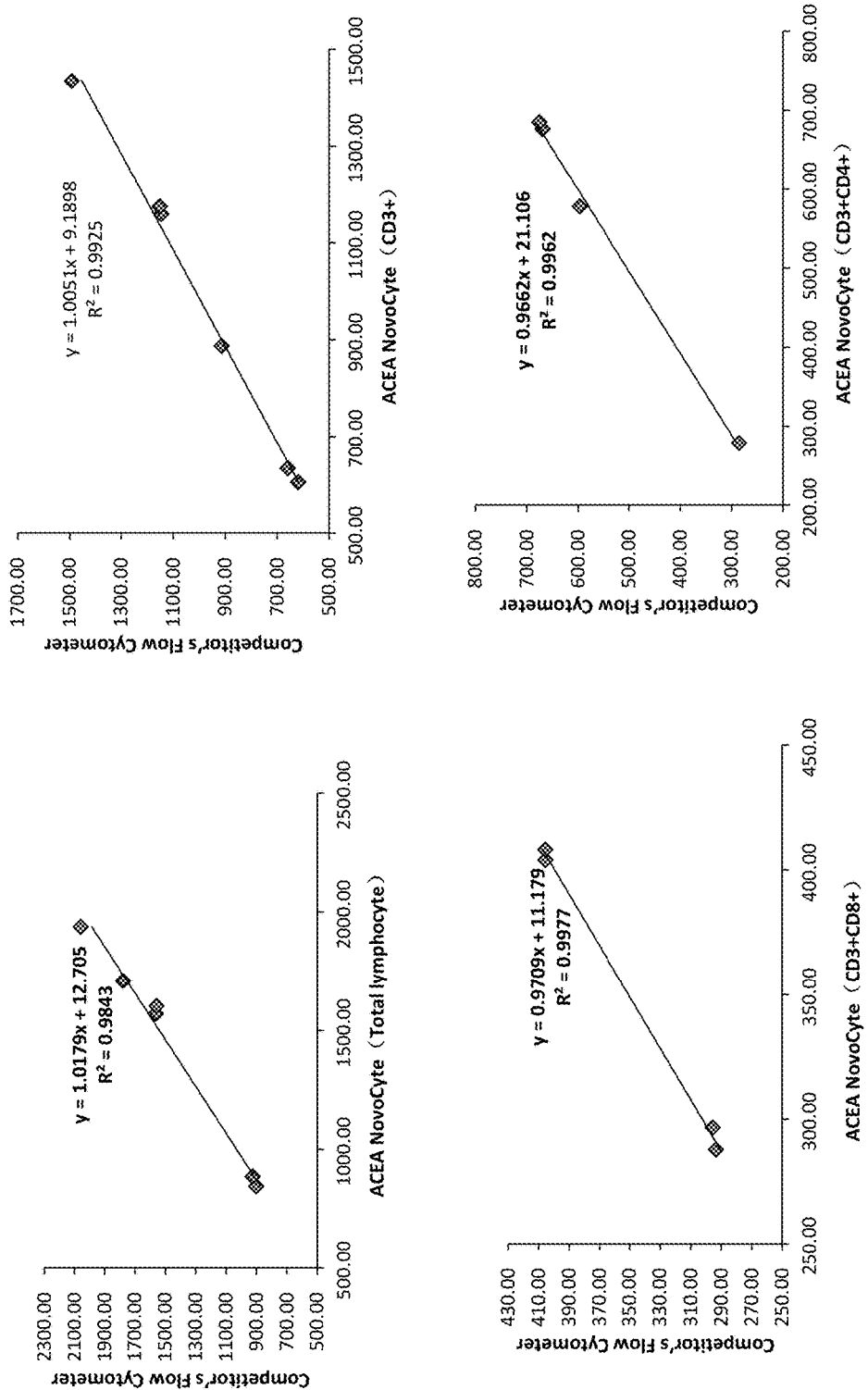
FIG. 20 shows a series of graphs comparing counts obtained from our flow cytometer (X-axis) and a competitor's flow cytometer (Y-axis) to demonstrate the close statistical relationship when counting total lymphocytes, CD3+ cells, CD3+/CD8+ cells, and CD3+/CD4+ cells in a control peripheral blood sample.

As shown in FIG. 15, the software provides convenient and easy to use compensation scroll bar 202 on each axis of each plot allowing rapid compensation, eliminating tedious and error prone adjustments, and which allows for real time compensation. FIG. 16 shows data from the cell cycle module, which incorporates the Watson Pragmatic model, which itself is a pragmatic model that makes no assumptions about the shape of S-phase distribution. Other analysis models, such as Dean-Jett-Fox model, can also be used for such cell cycle analysis. FIG. 17 demonstrates Levey-Jennings plots, which display daily cytometer QC results over time.

In still another related embodiment a flow cytometry method is provided, which includes providing flow cytometer or flow cytometer system as provided herein; labeling a sample of cells with a plurality of fluorescent labels; pumping the sample of cells through the flow channel; collecting flow cytometry data; and analyzing the flow cytometry data to determine the presence, absence or abundance of one or more of the plurality of fluorescent labels on or in cells of the sample.

EXAMPLES

Example 1: 10 Color Flow Cytometry Analysis of T-Lymphocytes

In this example, a flow cytometer was equipped with an optical engine configured for 10 color flow cytometry analysis. Beginning with a sample of human whole blood, red blood cells were lysed by incubation of the blood sample with a red blood cell lysis buffer. Cells were centrifuged and the supernatant discarded. The cells were resuspended, counted, and divided into equal populations for staining. Immunofluorescent staining of washed cells was conducted with labeled antibodies shown in TABLE 2.

TABLE 2

| BioLegend Cat# | Specificity | Label | Laser (Excitation) | FL Channel | Filter (Emission) |
|---|---|---|---|---|---|
| 356113 | CD25 | BV421 | 405 nm | VL1 | 445/45 |
| 317331 | CD3 | BV510 | 405 nm | VL2 | 530/30 |
| 353233 | CCR7 | BV650 | 405 nm | VL5 | 675/30 |
| 304139 | CD45RA | BV785 | 405 nm | VL6 | 780/60 |
| 82740 | CD4 | FITC | 488 nm | BL1 | 530/30 |
| 351304 | CD127 | PE | 488 nm | BL2 | 585/40 |
| 344707 | CD8 | PerCP | 488 nm | BL4 | 675/30 |
| 304229 | CD45RO | PE-Cy7 | 488 nm | BL5 | 780/60 |
| 304809 | CD62L | APC | 640 nm | RL1 | 675/30 |
| 304014 | CD45 | APC-Cy7 | 640 nm | RL2 | 780/60 |

TABLE 3 provides an overview of the staining approach. Staining was conducted in duplicates, which included a 10 color stain. Single color staining was also performed to adjust compensation according to standard flow cytometry practices. As further control, fluorescence minus one (FMO) staining was used to ensure proper interpretation of acquired fluorescence data. FMO contains all fluorochromes in a panel except for the one that is being measured, thereby ensuring that any spread of fluorochromes into the channel of interest is properly identified.

TABLE 3

|  | CD4 | CD25 | CD3 | CD197 | CD45RA | CD127 | CD8 | CD45RO | CD62L | CD45 |
|---|---|---|---|---|---|---|---|---|---|---|
| Sample 1 | 5 | 5 | 3 | 3 | 3 | 3 | 3 | 3 | 3 | 3 |
| Sample 2 | 5 | 5 | 3 | 3 | 3 | 3 | 3 | 3 | 3 | 3 |

T-lymphocytes were identified according to the presence of CD4 and CD8 and the following subpopulation of T-lymphocytes were identified according the presence, absence, or abundance of measured fluorescent signal from the immunostaining reagents: central memory T-cell, effector memory T-cell, naïve T-cell, regulatory T-cells (Treg). The populations were categorized according to TABLE 4.

TABLE 4

| Subpopulation | CD4+ | CD8+ |
|---|---|---|
| Central memory T | 45 RO+, 45RA−, CCR7+, CD62L+ | 45 RO+, 45RA−, CCR7+, CD62L+ |
| Effector memory T | 45 RO+, 45RA−, CCR7−; CD62L− | 45 RO+, 45RA−, CCR7−; CD62L− |
| Naïve T | 45RO−, 45RA+, CD62L+, CCR7+ | 45RO−, 45RA+, CD62L+, CCR7+ |
| Effector T | 45 RO−, 45RA+, CCR7−, CD62L− | 45 RO−, 45RA+, CCR7−, CD62L− |
| Treg | CD4+, CD25+, CD127−/low | 45 RO+, 45RA−, CCR7+, CD62L+ |

Figure 21:
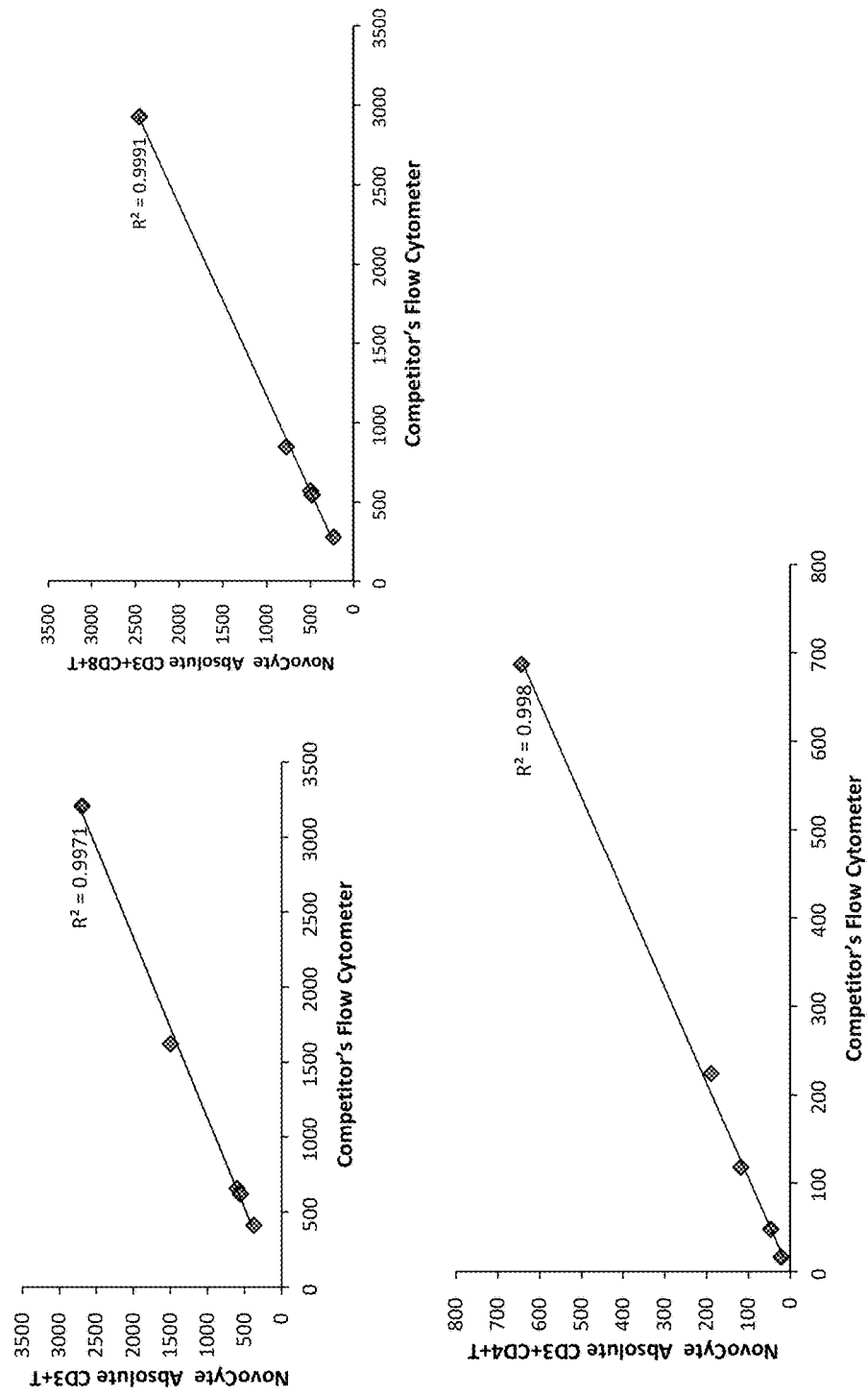
FIG. 21 shows a series of graphs comparing counts obtained from a competitor's flow cytometer (X-axis) and our flow cytometer (Y-axis) and to demonstrate the close statistical relationship when counting CD3+ cells and total lymphocytes, CD3+/CD8+ cells and total lymphocytes, and CD3+/CD4+ cells and total lymphocytes in a peripheral blood sample from a subject suffering from HIV.

As shown in FIG. 21, after acquiring the data, the following hierarchy of gating was used to identify T-cells. First, from a population of all cells, lymphocytes were identified according to CD45-APC-Cy7 vs side scatter (SSC), which accounted for 26.77% of the cell population. The lymphocyte population was plotted on FSC-A vs. FSC-H to selectively identify singlet populations vs. doublet populations. By more tightly gaiting the singlet population it was found that singlets represented 95.75% of the lymphocytes. Singlet lymphocytes were then plotted according to CD3-BV510 vs. side scatter (ssc) to identify 85.48% of the singlet lymphocytes as being CD3+. As shown in FIG. 22, CD3+ cells were then plotted according to CD4-FITC vs CD8-PerCP to identify the following subpopulations: 30.31% CD4−/CD8+; 62.98% CD4+/CD8−; 6.10% CD4−/CD8−; and 0.60% CD4+/CD8+. The CD4+/CD8− subpopulation was then plotted according to the following subplots: CD25-BV421 vs. CD127-PE (identifying Tregs as CD4+, CD25+, CD127−/low); and CD45RO-PE-Cy7 vs. CD45RA-BV785. Both CD45RO−, CD45RA+ (30.84% of CD4+/CD8−) and CD45RO+, CD45RA− (41.60% of CD4+/CD8−) subpopulations were plotted according to CCR7-BV650 vs. CD62L-APC. Naïve T-cells identified as CD62+, CCR7+ were found to represent 96.28% of CD45RA+/CD45RO− cells and effector T-cells were found to represent 1.73% of CD45RA+/CD45RO− cells. Central memory T-cells (Tcm), identified as CD62L+/CCR7+, were found to represent 63.54% of CD45RA−/CD45+ cells and effector memory T-cells (Tem) identified as CD62−/CCR7− were found to represent 19.81% of CD45RA−/CD45RO+ cells.

Example 2: Comparison of Absolute Cell Counting Between Our NovoCyte Flow Cytometer and a Competitor's Flow Cytometer To verify the counting accuracy of our flow cytometry system, we compared absolute counting results between our system to another commercially available system using commercially available QC blood, peripheral blood from a normal donor, and peripheral blood from a HIV patient.

Fresh peripheral human blood from normal donor (FB) and QC blood (QC) were stained with CD3-PereCP/CD4-FITC/CD8-PE in a reference-beads-containing tube. Data was acquired using our 2060 NovoCyte flow cytometer and a competitor's cytometer separately, and analyzed with our software. Measured cell concentrations are provided in TABLE 5, where each samples is numbered and designated either as QC blood (QC) or fresh peripheral human blood (FB) and values are provided as cell count per microliter (/uL).

TABLE 5

|  | Our NovoCyte Flow Cytometer | | | | Competitor's Flow Cytometer with Reference Beads | | | |
|---|---|---|---|---|---|---|---|---|
|  | Total lymphocyte | CD3+ | CD3+CD8+ | CD3+CD4+ | Total lymphocyte | CD3+ | CD3+CD8+ | CD3+CD4+ |
| S1-QC | 1937 | 1435 |  |  | 2057 | 1492 |  |  |
| S2-QC | 1570 | 1160 | 404 | 676 | 1563 | 1146 | 406 | 669 |
| S3-QC | 1605 | 1175 | 408 | 685 | 1558 | 1153 | 405 | 676 |
| S4-FB | 846 | 634 |  |  | 902 | 659 |  |  |
| S5-FB | 886 | 605 | 297 | 279 | 925 | 619 | 296 | 286 |
| S6-FB | 1710 | 888 | 288 | 578 | 1779 | 913 | 294 | 597 |

Regression analysis was performed to statistically estimate the relationship for our NovoCyte flow cytometer compared to the competitor's flow cytometer from measured counts from total lymphocytes; CD3+ cells; CD3+, CD8+ cells; and CD3+, CD4+ cells. We found that regression coefficients were over 98% indicating the close statistical relationship between the flow cytometers for counting. Representative results are shown in FIG. 23.

To further demonstrate potential applications for diagnostic applications we also compared our system to a competitor's flow cytometer using blood from patients suffering from human immunodeficiency virus (HIV), which is a lentivirus that causes the acquired immunodeficiency syndrome (AIDS). HIV patient peripheral blood was stained with CD3-PereCP/CD4-FITC/CD8-PE in a reference-beads-containing tube. Data was acquired using our 2060 NovoCyte flow cytometer and a competitor's cytometer separately, then analyzed with our software. Measured cell concentrations are provided in TABLE 6, where each samples is numbered S7-H to S11-H and values are provided as cell count concentration per microliter (/uL).

TABLE 6

| | Our NovoCyte Flow Cytometer | | | Competitor's Flow Cytometer with Reference Beads | | |
|---|---|---|---|---|---|---|
| | CD3+ | CD3+ CD4+ | CD3+ CD8+ | CD3+ | CD3+ CD4+ | CD3+CD8+ |
| S7-H | 603 | 22.4 | 500 | 658 | 16.1 | 572 |
| S8-H | 558 | 46.7 | 480 | 619 | 47.9 | 544 |
| S9-H | 1500 | 644 | 777 | 1622 | 686 | 848 |
| S10-H | 376 | 119 | 234 | 412 | 117 | 280 |
| S11-H | 2690 | 190 | 2453 | 3209 | 224 | 2927 |

Regression analysis was performed to statistically estimate the relationship for our NovoCyte flow cytometer compared to the competitor's flow cytometer from measured counts from CD3+ cells; CD3+/CD4+ cells; and CD3+/CD8+ cells. We found that regression coefficients were over 99% indicating the close statistical relationship between the flow cytometers for counting. Representative results are shown in FIG. 24.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An optical engine for use in a bench top flow cytometer, the optical engine comprising:
 a) a set of lasers, each tuned to a wavelength suited for excitation of fluorescent molecules;
 b) a different set of beam shaping optics for each laser, wherein each set comprises two lenses, wherein a first lens adjustably focuses a beam horizontally along an x-axis to a same horizontal position and a second lens vertically adjusts the beam along a y-axis to a different vertical position along a same plane, wherein the plane is characterized as a flow path through a flow cell of the flow cytometer;
 c) collection optics for collecting fluorescence from the flow cell;
 d) filtration optics that filter the collected fluorescence from the flow cell into different filter channels according to wavelength ranges; and
 e) a detector for each filter channel that converts the filtered fluorescence to electrical signals, wherein electrical signals are processed so that the fluorescence from each laser at the different vertical positions is distinguished at the same detector.

2. The optical engine according to claim 1, wherein the set of lasers comprises three lasers, each tuned to a different wavelength and directed to a different vertical position of the plane thereby providing three distinct vertical positions along the flow cell.

3. The optical engine according to claim 2, wherein the vertical positions are separated by 80 μm.

4. The optical engine according to claim 2, comprising 13 fluorescence channels from a single sample passing through the flow cell.

5. The optical engine according to claim 1, wherein the set of beam shaping optics comprise a cylindrical lens or a Powell lens.

6. The optical engine according to claim 1, wherein the collection optics comprise a half ball lens followed by a doublet lens.

7. The optical engine according to claim 1, wherein the filtration optics comprise a component selected from the group consisting of a dichroic mirror, a bandpass filter, and a focusing lens.

8. The optical engine according to claim 1, where the filter channels comprise the following wavelengths: 780/60 nm, 615/24 nm, 530/30 nm, 445/45 nm, 585/40 or 572/28 nm and 675/30 nm.

9. The optical engine according to claim 1, further comprising a forward scatter (FSC) detector, a FSC focusing lens, and an obscuration bar.

10. The optical engine according to claim 9, wherein the obscuration bar is diamond shaped or has a rectangular shape with its horizontal dimension being the same as or larger than its vertical dimension.

11. The optical engine according to claim 9, wherein the perimeter of the obscuration bar follows a contour of a light intensity distribution plot, optionally within the 0.1% contour line.

12. The optical engine according to claim 11, wherein the obscuration bar blocks 99% of unscattered light from detection by the FSC detector.

13. The optical engine according to claim 1, further comprising a housing configured to house optical engine components, the optical engine components comprising the set of lasers, the beam shaping optics, the collection optics, the filtration optics, and the detectors, wherein a same housing is configured for interchangeability of different lasers, lenses, mirrors, filters, and detectors.

14. The optical engine according to claim 1, further comprising the flow cell.

15. The optical engine according to claim 1, wherein distinguishing the fluorescence at the same detector from different lasers at the different vertical positions is achieved through either a forward-scatter-coincidence method or a laser-modulation and fluorescence-demodulation method, or combination of both methods.

16. An optical engine for use in a bench top flow cytometer, the optical engine comprising:
 a) a set of lasers, each tuned to a wavelength suited for excitation of fluorescent molecules;
 b) a different set of beam shaping optics for each laser, wherein each set comprises two lenses to adjustably focus a beam horizontally along an x-axis to a same horizontal position and vertically along a y-axis to a different vertical position along a same plane, wherein the plane is characterized as a flow path through a flow cell of the flow cytometer;
 c) collection optics for collecting fluorescence from the flow cell, wherein the collection optics comprise a half ball lens followed by a doublet lens;
 d) filtration optics that filter the collected fluorescence from the flow cell into different filter channels according to wavelength ranges; and
 e) a detector for each filter channel that converts the filtered fluorescence to electrical signals, wherein electrical signals are processed so that the fluorescence from each laser at the different vertical positions is distinguished at the same detector.

17. The optical engine according to claim 16, wherein the set of lasers comprises three lasers, each tuned to a different wavelength and directed to a different vertical position of the plane thereby providing three distinct vertical positions along the flow cell.

18. The optical engine according to claim 16, further comprising a forward scatter (FSC) detector, a FSC focusing lens, and an obscuration bar.

19. The optical engine according to claim 18, wherein the perimeter of the obscuration bar follows a contour of a light intensity distribution plot, optionally within the 0.1% contour line.

20. The optical engine according to claim 16, wherein distinguishing the fluorescence at the same detector from different lasers at the different vertical positions is achieved through either a forward-scatter-coincidence method or a laser-modulation and fluorescence-demodulation method, or combination of both methods.

\* \* \* \* \*